United States Patent
Diehl et al.

(10) Patent No.: US 10,150,988 B2
(45) Date of Patent: Dec. 11, 2018

(54) MULTIPLEXED IN SITU MOLECULAR ANALYSES AND PROGRAMMABLE MOLECULAR PROBES FOR REGULATED SINGLE AMPLIFICATION

(71) Applicant: William Marsh Rice University, Houston, TX (US)

(72) Inventors: Michael Diehl, Houston, TX (US); Jan Zimak, Houston, TX (US); Ryan Schweller, Houston, TX (US); Edward B. Samson, Houston, TX (US); Dzifa Y. Duose, Houston, TX (US)

(73) Assignee: WILLIAM MARSH RICE UNIVERSITY, Houston, TX (US)

( * ) Notice: Subject to any disclaimer, the term of this patent is extended or adjusted under 35 U.S.C. 154(b) by 644 days.

(21) Appl. No.: 14/421,504

(22) PCT Filed: Aug. 13, 2013

(86) PCT No.: PCT/US2013/054798
§ 371 (c)(1),
(2) Date: Feb. 13, 2015

(87) PCT Pub. No.: WO2014/028538
PCT Pub. Date: Feb. 20, 2014

(65) Prior Publication Data
US 2016/0002704 A1    Jan. 7, 2016

Related U.S. Application Data

(60) Provisional application No. 61/682,522, filed on Aug. 13, 2012.

(51) Int. Cl.
C12Q 1/68 (2018.01)
C12Q 1/682 (2018.01)
C12Q 1/6816 (2018.01)
C12Q 1/6841 (2018.01)

(52) U.S. Cl.
CPC .......... *C12Q 1/682* (2013.01); *C12Q 1/6816* (2013.01); *C12Q 1/6841* (2013.01)

(58) Field of Classification Search
None
See application file for complete search history.

(56) References Cited

PUBLICATIONS

Duose et al., "Configuring robust DNA strand displacement reactions for in situ molecular analyses," Nucleic Acids Res. 2012, 40:3289-3298, published online Dec. 11, 2011.*
Schweitzer et al., "Combining nucleic acid amplification and detection," Curr. Opin. Biotechnol. 2001, 12:21-27.*
Choi, Harry M.T. et al., "Programmable in situ Amplification for Multiplexed Imaging of mRNA Expression." *Nat Biotechnol*, Nov. 2010, 28(11); pp. 1208-1212.
Duose, Dzifa Y et al., "Multiplexed and Reiterative Fluorescence Labeling by DNA Circuitry." *Bioconjugate Chemistry*, Dec. 15, 2010, vol. 21, No. 12, pp. 2327-2331.
Duose, Dzifa Y et al., "Configuring robust DNA strand displacement reactions for in situ molecular analysis." *Nucleic Acids Research, Oxford University Press*, Apr. 1, 2012, vol. 40, No. 2, pp. 3289-4962.
Schweller, Ryan M. et al., "Multiplexed In Situ Immunofluorescence Using Dynamic DNA Complexes." *Angewandte Chemie International Edition*, Aug. 15, 2012, vol. 51, No. 37, pp. 9292-9296.
Schweitzer, Barry et al., "Combining Nucleic Acid Amplification and Detection." *Current Opinion in Biotechnology*, Feb. 1, 2001, vol. 12, No. 1, pp. 21-27.
Zang, David Yu et al., "Engineering Entropy-Driven Reactions and Networks Catalyzed by DNA." *Science*, Nov. 16, 2007, vol. 318, pp. 1121-1125; Erratum Post Date Dec. 18, 2009, p. 1.
Zimak, Jan et al., "Programming in Situ Immunofluorescence Intensities through Interchangeable Reactions of Dynamic DNA Complexes." *Chembiochem*, Nov. 20, 2012, vol. 13, No. 18, pp. 2722-2728.
PCT International Search Report and Written Opinion issued in International Application No. PCT/US2013/054798, dated Apr. 11, 2014.
International Preliminary Report on Patentability issued in International Application No. PCT/US2013/054798, dated Feb. 17, 2015.

* cited by examiner

*Primary Examiner* — Kaijiang Zhang
(74) *Attorney, Agent, or Firm* — Parker Highlander PLLC

(57) ABSTRACT

The present invention generally relates to methods for detecting a target in a sample; methods for modulating the reporting intensity of a labeled target in a sample of fixed cells or tissues; methods for detecting the location of at least two targets in a sample; and related compositions.

12 Claims, 10 Drawing Sheets
Specification includes a Sequence Listing.

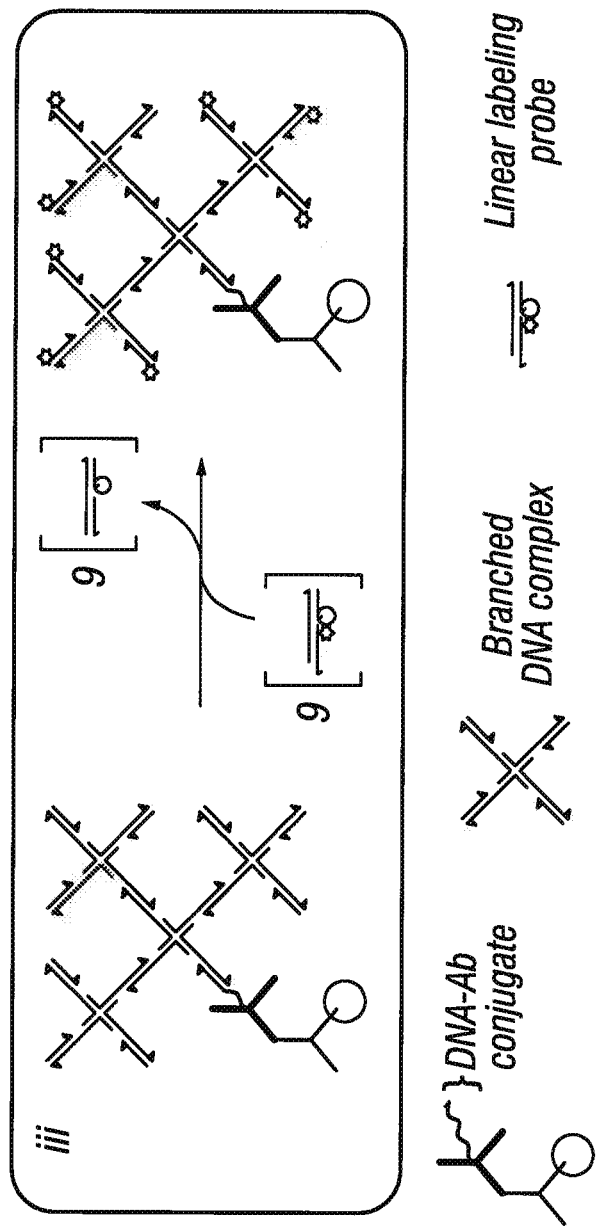

SEQUENCE LISTING

<160> NUMBER OF SEQ ID NOS: 33

<210> SEQ ID NO 1
<211> LENGTH: 36
<212> TYPE: DNA
<213> ORGANISM: Artificial Sequence
<220> FEATURE:
<223> OTHER INFORMATION: Synthetic oligonucleotide - PS3 I & PS4 I
<220> FEATURE:
<221> NAME/KEY: 5' Amino Modifier C6
<222> LOCATION: (1)..(1)

<400> SEQUENCE: 1
tttttttttt ggccaccgag acaatacgca ggaccc                                36

<210> SEQ ID NO 2
<211> LENGTH: 36
<212> TYPE: DNA
<213> ORGANISM: Artificial Sequence
<220> FEATURE:
<223> OTHER INFORMATION: Synthetic oligonucleotide - PS1 I & PS2 I
<220> FEATURE:
<221> NAME/KEY: 5' Amino Modifier C6
<222> LOCATION: (1)..(1)

<400> SEQUENCE: 2
tttttttttt gtgtaccgga aacatcggcg aattag                                36

<210> SEQ ID NO 3
<211> LENGTH: 36
<212> TYPE: DNA
<213> ORGANISM: Artificial Sequence
<220> FEATURE:
<223> OTHER INFORMATION: Synthetic oligonucleotide - PS5 I & PS6 I
<220> FEATURE:
<221> NAME/KEY: 5' Amino Modifier C6
<222> LOCATION: (1)..(1)

<400> SEQUENCE: 3
tttttttttt ttacgcggta cacctgtgcg gatata                                36

<210> SEQ ID NO 4
<211> LENGTH: 36
<212> TYPE: DNA
<213> ORGANISM: Artificial Sequence
<220> FEATURE:
<223> OTHER INFORMATION: Synthetic oligonucleotide - PS3 I & PS4 I
<220> FEATURE:
<221> NAME/KEY: 5'Hexynyl
<222> LOCATION: (1)..(1)

<400> SEQUENCE: 4
tttttttttt ggccaccgag acaatacgca ggaccc                                36

<210> SEQ ID NO 5
<211> LENGTH: 36
<212> TYPE: DNA
<213> ORGANISM: Artificial Sequence
<220> FEATURE:
<223> OTHER INFORMATION: Synthetic oligonucleotide - PS1 I & PS2 I
<220> FEATURE:
<221> NAME/KEY: 5' Hexynyl
<222> LOCATION: (1)..(1)

<400> SEQUENCE: 5
tttttttttt gtgtaccgga aacatcggcg aattag                                36

<210> SEQ ID NO 6

```
<211> LENGTH: 36
<212> TYPE: DNA
<213> ORGANISM: Artificial Sequence
<220> FEATURE:
<223> OTHER INFORMATION: Synthetic oligonucleotide - PS5 I & PS6 I
<220> FEATURE:
<221> NAME/KEY: 5' Hexynyl
<222> LOCATION: (1)..(1)

<400> SEQUENCE: 6
tttttttttt ttacgcggta cacctgtgcg gatata                               36

<210> SEQ ID NO 7
<211> LENGTH: 66
<212> TYPE: DNA
<213> ORGANISM: Artificial Sequence
<220> FEATURE:
<223> OTHER INFORMATION: Synthetic oligonucleotide - BC1-1

<400> SEQUENCE: 7
acttaatgaa cgctagcatc acgccggtac ttacaaggta tagtatacca ggagggcttg     60
tcaacc                                                                66

<210> SEQ ID NO 8
<211> LENGTH: 66
<212> TYPE: DNA
<213> ORGANISM: Artificial Sequence
<220> FEATURE:
<223> OTHER INFORMATION: Synthetic oligonucleotide - BC1-2

<400> SEQUENCE: 8
ttgtaagtac cggcgtgaga gaccgttaag ctacctgcga gtgtaccgga aacatcggcg     60
aattag                                                                66

<210> SEQ ID NO 9
<211> LENGTH: 66
<212> TYPE: DNA
<213> ORGANISM: Artificial Sequence
<220> FEATURE:
<223> OTHER INFORMATION: Synthetic oligonucleotide - BC1-3

<400> SEQUENCE: 9
aggtagctta acggtctcat aggcacagat cgaaccgctc gtgtaccgga aacatcggcg     60
aattag                                                                66

<210> SEQ ID NO 10
<211> LENGTH: 66
<212> TYPE: DNA
<213> ORGANISM: Artificial Sequence
<220> FEATURE:
<223> OTHER INFORMATION: Synthetic oligonucleotide - BC1-4

<400> SEQUENCE: 10
ggttcgatct gtgcctattg ctagcgttca ttaagtgcca gtgtaccgga aacatcggcg     60
aattag                                                                66

<210> SEQ ID NO 11
<211> LENGTH: 28
<212> TYPE: DNA
<213> ORGANISM: Artificial Sequence
<220> FEATURE:
<223> OTHER INFORMATION: Synthetic oligonucleotide - BC1-5

<400> SEQUENCE: 11
```

```
aaggtatagt ataccaggag ggcttgtc                                          28

<210> SEQ ID NO 12
<211> LENGTH: 26
<212> TYPE: DNA
<213> ORGANISM: Artificial Sequence
<220> FEATURE:
<223> OTHER INFORMATION: Synthetic oligonucleotide - BC1-6

<400> SEQUENCE: 12
aaaaaaaatt cgccgatgtt tccgac                                            26

<210> SEQ ID NO 13
<211> LENGTH: 72
<212> TYPE: DNA
<213> ORGANISM: Artificial Sequence
<220> FEATURE:
<223> OTHER INFORMATION: Synthetic oligonucleotide - BC2-1

<400> SEQUENCE: 13
cactgttcac ttcacgcttt ggtcgcttcc acgaacgagc atccatgtga gggcgcttat       60
tgtattcaga ga                                                           72

<210> SEQ ID NO 14
<211> LENGTH: 68
<212> TYPE: DNA
<213> ORGANISM: Artificial Sequence
<220> FEATURE:
<223> OTHER INFORMATION: Synthetic oligonucleotide - BC2-2

<400> SEQUENCE: 14
gttcgtggaa gcgaccaata ctcgtttcac cgtcaacctg cggtctggcg aatgtagcgt       60
atgtgctc                                                                68

<210> SEQ ID NO 15
<211> LENGTH: 68
<212> TYPE: DNA
<213> ORGANISM: Artificial Sequence
<220> FEATURE:
<223> OTHER INFORMATION: Synthetic oligonucleotide - BC2-3

<400> SEQUENCE: 15
ttgacggtga aacgagtaat tgacgtatgc tggttccgag aggtctggcg aatgtagcgt       60
atgtgctc                                                                68

<210> SEQ ID NO 16
<211> LENGTH: 68
<212> TYPE: DNA
<213> ORGANISM: Artificial Sequence
<220> FEATURE:
<223> OTHER INFORMATION: Synthetic oligonucleotide - BC2-4

<400> SEQUENCE: 16
gaaccagcat acgtcaatag cgtgaagtga acagtggaat gtgtctggcg aatgtagcgt       60
atgtgctc                                                                68

<210> SEQ ID NO 17
<211> LENGTH: 26
<212> TYPE: DNA
<213> ORGANISM: Artificial Sequence
<220> FEATURE:
<223> OTHER INFORMATION: Synthetic oligonucleotide - BC2-5

<400> SEQUENCE: 17
```
caaatacaat aagcgccctc gtgcaa                                              26

<210> SEQ ID NO 18
<211> LENGTH: 26
<212> TYPE: DNA
<213> ORGANISM: Artificial Sequence
<220> FEATURE:
<223> OTHER INFORMATION: Synthetic oligonucleotide - BC2-6

<400> SEQUENCE: 18
gtatgagcac atacgctaca ttcgtt                                              26

<210> SEQ ID NO 19
<211> LENGTH: 72
<212> TYPE: DNA
<213> ORGANISM: Artificial Sequence
<220> FEATURE:
<223> OTHER INFORMATION: Synthetic oligonucleotide - BC3-1

<400> SEQUENCE: 19
gaatccgaga aggtcgaatc gcacgacatt ccggtgattt ggacgcaggc acatacgcta        60
cattcgccag ac                                                            72

<210> SEQ ID NO 20
<211> LENGTH: 68
<212> TYPE: DNA
<213> ORGANISM: Artificial Sequence
<220> FEATURE:
<223> OTHER INFORMATION: Synthetic oligonucleotide - BC3-2

<400> SEQUENCE: 20
caccggaatg tcgtgcgagc gagaaatcac agcatacgcg ttttacgcgg tacacctgtg        60
cggatata                                                                 68

<210> SEQ ID NO 21
<211> LENGTH: 68
<212> TYPE: DNA
<213> ORGANISM: Artificial Sequence
<220> FEATURE:
<223> OTHER INFORMATION: Synthetic oligonucleotide - BC3-3

<400> SEQUENCE: 21
tatgctgtga tttctcgctg acaccaaggc aaccatgatc tattacgcgg tacacctgtg        60
cggatata                                                                 68

<210> SEQ ID NO 22
<211> LENGTH: 68
<212> TYPE: DNA
<213> ORGANISM: Artificial Sequence
<220> FEATURE:
<223> OTHER INFORMATION: Synthetic oligonucleotide - BC3-4

<400> SEQUENCE: 22
atggttgcct tggtgtcatt cgaccttctc ggattcgttt agttacgcgg tacacctgtg        60
cggatata                                                                 68

<210> SEQ ID NO 23
<211> LENGTH: 26
<212> TYPE: DNA
<213> ORGANISM: Artificial Sequence
<220> FEATURE:
<223> OTHER INFORMATION: Synthetic oligonucleotide - BC3-5

```
<400> SEQUENCE: 23
aacgaatgta gcgtatgtgc tcatac                                          26

<210> SEQ ID NO 24
<211> LENGTH: 29
<212> TYPE: DNA
<213> ORGANISM: Artificial Sequence
<220> FEATURE:
<223> OTHER INFORMATION: Synthetic oligonucleotide - BC3-6

<400> SEQUENCE: 24
aaaaaaaaat atccgcacag gtgtaccat                                       29

<210> SEQ ID NO 25
<211> LENGTH: 18
<212> TYPE: DNA
<213> ORGANISM: Artificial Sequence
<220> FEATURE:
<223> OTHER INFORMATION: Synthetic oligonucleotide - FQ
<220> FEATURE:
<221> NAME/KEY: 3' Iowa Black re quencher
<222> LOCATION: (18)..(18)

<400> SEQUENCE: 25
cgtaatagcg ctagtctc                                                   18

<210> SEQ ID NO 26
<211> LENGTH: 33
<212> TYPE: DNA
<213> ORGANISM: Artificial Sequence
<220> FEATURE:
<223> OTHER INFORMATION: Synthetic oligonucleotide - PS1 & PS3 D
<220> FEATURE:
<221> NAME/KEY: 5' Cy3
<222> LOCATION: (1)..(1)

<400> SEQUENCE: 26
tttcttgtca attcgccgat gtttccggta cac                                  33

<210> SEQ ID NO 27
<211> LENGTH: 44
<212> TYPE: DNA
<213> ORGANISM: Artificial Sequence
<220> FEATURE:
<223> OTHER INFORMATION: Synthetic oligonucleotide - PS1 & PS3 L

<400> SEQUENCE: 27
gtcggaaaca tcggcgaatt tttttgaga ctagcgctat tacg                       44

<210> SEQ ID NO 28
<211> LENGTH: 33
<212> TYPE: DNA
<213> ORGANISM: Artificial Sequence
<220> FEATURE:
<223> OTHER INFORMATION: Synthetic oligonucleotide - PS2 & PS4 D
<220> FEATURE:
<221> NAME/KEY: 5' Cy3
<222> LOCATION: (1)..(1)
<220> FEATURE:
<221> NAME/KEY: 3' Cy3Sp
<222> LOCATION: (33)..(33)

<400> SEQUENCE: 28
tttcttgtca attcgccgat gtttccggta cac                                  33

<210> SEQ ID NO 29
<211> LENGTH: 44
```

```
<212> TYPE: DNA
<213> ORGANISM: Artificial Sequence
<220> FEATURE:
<223> OTHER INFORMATION: Synthetic oligonucleotide - PS2 & PS4 L
<220> FEATURE:
<221> NAME/KEY: 5' Cy3
<222> LOCATION: (1)..(1)

<400> SEQUENCE: 29
gtcggaaaca tcggcgaatt tttttttgaga ctagcgctat tacg         44

<210> SEQ ID NO 30
<211> LENGTH: 33
<212> TYPE: DNA
<213> ORGANISM: Artificial Sequence
<220> FEATURE:
<223> OTHER INFORMATION: Synthetic oligonucleotide - PS5 D
<220> FEATURE:
<221> NAME/KEY: 5' Cy3
<222> LOCATION: (1)..(1)

<400> SEQUENCE: 30
tttcaaacgt atccgcacag gtgtaccgcg taa                      33

<210> SEQ ID NO 31
<211> LENGTH: 50
<212> TYPE: DNA
<213> ORGANISM: Artificial Sequence
<220> FEATURE:
<223> OTHER INFORMATION: Synthetic oligonucleotide - PS5 L

<400> SEQUENCE: 31
atggtacacc tgtgcggata ttttttttttt ttgagactag cgctattacg   50

<210> SEQ ID NO 32
<211> LENGTH: 33
<212> TYPE: DNA
<213> ORGANISM: Artificial Sequence
<220> FEATURE:
<223> OTHER INFORMATION: Synthetic oligonucleotide - PS6 D
<220> FEATURE:
<221> NAME/KEY: 5' Cy3
<222> LOCATION: (1)..(1)
<220> FEATURE:
<221> NAME/KEY: 3' Cy3Sp
<222> LOCATION: (33)..(33)

<400> SEQUENCE: 32
tttcaaacgt atccgcacag gtgtaccgcg taa                      33

<210> SEQ ID NO 33
<211> LENGTH: 50
<212> TYPE: DNA
<213> ORGANISM: Artificial Sequence
<220> FEATURE:
<223> OTHER INFORMATION: Synthetic oligonucleotide - PS6 L

<400> SEQUENCE: 33
atggtacacc tgtgcggata ttttttttttt ttgagactag cgctattacg   50
```

MULTIPLEXED IN SITU MOLECULAR ANALYSES AND PROGRAMMABLE MOLECULAR PROBES FOR REGULATED SINGLE AMPLIFICATION

CROSS-REFERENCE TO RELATED APPLICATIONS

This application is a national phase application under 35 U.S.C. § 371 of International Application No. PCT/US2013/054798, filed Aug. 13, 2013, claims the benefit of U.S. Provisional Application No. 61/682,522, filed Aug. 13, 2012, the entire content of which is herein incorporated by reference in its entirety.

STATEMENT REGARDING FEDERALLY SPONSORED RESEARCH OR DEVELOPMENT

The invention was made with government support under Grant Number MCB-0643832 awarded by the National Science Foundation. The government has certain rights to this invention.

The invention was made with government support under Grant Number R21CA147912 awarded by the National Institutes of Health. The government has certain rights to this invention.

The invention was made with government support under Grant Number T32EB009379 awarded by the National Institutes of Health. The government has certain rights to this invention.

The invention was made with government support under Grant Number W81XWH-09-2-0139 awarded by the Army Medical Research and Material Command. The government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is CLIENT NAME_SEQ_LIST_ST25.txt. The text file is 9 KB, was created on Aug. 12, 2013, and is being submitted electronically via EFS-Web.

BACKGROUND OF THE INVENTION

Technical Field

The present invention generally relates to molecular imaging compositions, and methods of using the same, and methods of signal amplification. More particularly, the invention relates to multiplexed and programmable imaging compositions for high resolution analysis of cell physiology, phenotype, and molecular pathway visualization.

Description of the Related Art

The chemical amplification of molecular recognition events is critical to numerous in situ analyses of proteins, RNA and other biomolecular species within cells and tissues. Such capabilities are often necessary to extend the dynamic range of an imaging technique so that dilute molecular targets can be visualized within a specimen. Several enzymatic signal amplification strategies have been established that allow large numbers of active dye molecules to be localized to their primary target including tyramide signal amplification (TSA) and polymerization chain reaction-based methods such as rolling circle amplification (RCA).

Non-enzymatic amplification procedures based on the triggered polymerization of nucleic acid hairpin devices have also been developed explicitly for the in situ detection of mRNA targets. Each of these methods offer high signal amplification gains and can be used to detect low level molecular species. However, they generally offer limited control over final amplification levels since they rely on chemical reactions that need to be timed and/or quenched in order to arrest the signal amplification process. Moreover, the rates of these chemical reactions likely depend on the local concentrations and chemical environment surrounding their primary targets, which can, in turn, lead to sample- and local context-dependent modulation of signal amplification rates and levels in different settings. In addition to increased detection sensitivities, a variety of molecular analyses stand to benefit from the development of convergent amplification strategies that can produce defined and uniform amplification gains that can be tuned predicatively to regulate reporting levels.

Such capabilities are important for comparative analyses of target levels within and across different biological samples since potential variability in protein staining can compromise abilities to assess functionally significant changes in target levels. Furthermore, the intensities of the reporting molecules must often be regulated for multiplexed molecular imaging strategies where multiple types of fluorescent reporting molecules are used to detect different molecular targets within a sample. The emission spectra of most fluorophores are relatively broad and exhibit a significant degree of spectral overlap. Since these properties can lead to appreciable bleed-through of target signals between a microscope's spectral channels, the levels of multiple fluorophores in multi-color imaging assays must often be balanced appropriately so as to avoid intense staining of one particular range of a hyperspectral imaging system and to ensure the detection of dilute targets is not influenced by noise generated by spatially and spectrally overlapping signals stemming from more abundant targets within a sample.

These issues are typically addressed by diluting the recognition reagents of the more intense targets within a sample to achieve more equitable intensity distributions among each overlapping target. Although it would clearly be beneficial to balance maker intensities by amplifying the less intense signals, the lack of control over amplification levels provided by existing technologies generally limits their use in these applications.

SUMMARY OF THE INVENTION

Certain embodiments of the invention relate to methods for visualizing molecular targets within a biological sample. Additional embodiments of the invention relate to methods for localization of molecular targets within a biological sample. Particular embodiments of the invention relate to methods for localization of multiple targets within a biological sample. Other embodiments of the invention provide methods for using color-time-sequence codes to identify multiple target molecules and their locations within a sample without the need to employ chemical (e.g., the use of denaturants) or optical treatments (e.g., photobleaching) to remove targeting agents from a sample. Further embodiments of the invention may be used to controllably adapt the color and/or functionalities of a label on a particular target so that cells or tissue samples can be inspected using conventional microscopy techniques and then relabeled to facilitate highly-multiplexed molecular analyses of molecular targets, such as proteins and related biomacromolecules.

In certain embodiments of the invention, the dynamic DNA complexes are designed to be used interchangeably both to generate structurally-organized, branched or dendritic reporting complexes that possess different number of terminal branches and to control the number of dye molecules coupled to each branch. Complexes can be detected using any conventional microscopy techniques (e.g., epi-fluorescence and confocal microscopy).

The invention also provides methods for tuning, or controlling, the reporting intensities of dyes, such as fluorophores, used to label molecular targets, such as proteins, by controlling the number and type of dyes complexed to the target through the use of dynamic DNA complexes, including branched, dendritic, and multi-generational dynamic DNA complexes. Such tuning methods can be used with any suitable imaging application, including those using multi-color, epi-fluorescence, standard confocal, and/or hyper-spectral microscopies.

The invention also provides methods for identifying the locations of various molecular targets in a sample by repeated labeling and imaging of molecular targets with multiple dyes in a predetermined order to provide each target with a distinctive color-time-sequence (CTS) code that may be used to identify the target by determining the combination of colors, or dyes, that co-localize in a merged image of the sample and the time-sequence that they appeared. In particular embodiments of the invention, the present invention is directed to methods to visualize many different molecular targets within a biological sample including but not limited to 2, 3, 4, 5, 6, 7, 8, 9, 10, 20, 30, 40, 50, 60, 70, 80, 90, or 100 or more targets.

Any microscopy technique that is capable of detecting and localizing single fluorophores within a sample may be used with any of the embodiments of the invention. A sample may first be imaged using standard imaging techniques that do not provide single-molecule detection capabilities, and then subsequently imaged using any of the embodiments described herein, such as the CTS method. This approach allows users to define regions of interest within a sample that can then be selected for highly multiplexed CTS analyses.

Certain embodiments of the invention provide for a method for detecting a target in a sample, the method comprising: a) complexing a target-recognition agent to the target, wherein the target-recognition agent comprises a polynucleotide to form a polynucleotide-target complex; b) reacting the polynucleotide-target complex via strand displacement with a branched or dendritic dynamic DNA complex to create a dynamic DNA-target complex; and c) reacting the dynamic DNA-target complex via strand displacement with a first probe comprising at least one dye and a polynucleotide to form a first labeling complex. In particular embodiments of the invention, the first probe from a first labeling complex is displaced by a second probe via strand displacement to form a second labeling complex. In further embodiments of the invention, the first probe from a first labeling complex is stripped from the labeling complex via strand displacement, and the polynucleotide-target complex reacted via strand displacement with a second probe comprising at least one dye and a polynucleotide to form a second labeling complex. In particular embodiments of the invention, the branched or dendritic dynamic DNA complex comprises a polynucleotide sequence partially or completely complementary to the polynucleotide complexed to the target. In further embodiments of the invention, the branched or dendritic dynamic DNA complex comprises a polynucleotide sequence partially or completely complementary to the polynucleotide of the probe.

Other embodiments of the invention provide for a method for detecting a target in a sample, the method comprising: a) complexing a target-recognition agent to the target, wherein the target-recognition agent comprises a polynucleotide, to form a polynucleotide-target complex; b) reacting the polynucleotide-target complex via strand displacement with a branched or dendridic dynamic DNA complex to create a dynamic DNA-target complex; c) reacting the dynamic DNA-target complex via strand displacement with at least one branched or dendridic structure dynamic DNA complex to form a multi-generation dynamic DNA-target complex; d) reacting the multi-generation dynamic DNA-target complex via strand displacement with a probe comprising at least one dye and a polynucleotide to form a labeling complex. In particular embodiments of the invention, the branched or dendritic dynamic DNA complex comprises a polynucleotide sequence partially or completely complementary to the polynucleotide complexed to the target. In further embodiments of the invention, the multi-generation dynamic DNA complex has a polynucleotide sequence partially or completely complementary to the polynucleotide of the probe.

Particular embodiments of the invention provide for a method for modulating the reporting intensity of a labeled target in a sample of fixed cells or tissues, the method comprising: a) complexing a target-recognition agent to the target, wherein the target-recognition agent comprises a polynucleotide to form a polynucleotide-target complex; b) reacting the polynucleotide-target complex via strand displacement with a branched or dendridic dynamic DNA complex to create a dynamic DNA-target complex; c) reacting the dynamic DNA-target complex via strand displacement with a first probe comprising at least one dye and a polynucleotide to form a first labeling complex; d) measuring the reporting intensity of the first labeling complex; and e) contacting the sample with a second probe comprising at least one dye and a polynucleotide, such that the second probe displaces the first probe via strand displacement to form a second labeling complex and the second probe carries a different number and/or type of dye molecule than the first probe.

Further embodiments of the invention provide for a method for detecting the location of at least two targets in a sample, wherein each target is labeled and detected by a method comprising: a) complexing a target-specific-recognition agent with the target, wherein the target-specific-recognition agent comprises a polynucleotide; b) reacting the target via strand displacement with a first dynamic DNA complex comprising at least one dye and a polynucleotide to form a first-labeling complex; c) detecting the dye present in the sample; d) reacting the first-labeling complex via strand displacement with a second dynamic DNA complex comprising at least one dye and a polynucleotide wherein the second dynamic DNA complex replaces the first dynamic DNA complex via strand displacement to form a second-labeling complex; e) detecting the dye present in the sample. In still further embodiments of the invention, the labeling complex can be relabeled again, including, but not limited to, at least once more, at least twice more, at least three times more, at least four times more, at least five times more, at least six times more, at least seven times more, at least eight times more, at least nine times more, and at least ten times more. In particular embodiments of the invention, the dye is detected by visualizing the sample via any suitable microscopy technique in order to determine the location of the dye-labeled target on a single molecule level. In further embodiments of the invention, the target-specific-recognition agent comprises a polynucleotide sequence partially or completely complementary to the polynucleotide of the probe. In particular embodiments of the invention, the relabeling occurs at least once with an additional dynamic DNA complex comprising at least one dye and a nucleic acid, wherein each target is labeled with a sequence of dyes corresponding to a predetermined color-time sequence code, and wherein no two targets have the same color-time sequence code.

Further embodiments of the invention include a composition comprising: a) at least one target recognition agent comprising a single stranded polynucleotide; b) at least one probe comprising one or more fluorescent dyes, wherein the probe comprises a polynucleotide sequence partially or completely complementary to the single stranded polynucleotide of step a). In certain embodiments, the target recognition agent comprises an antibody or antigen binding fragment thereof, a nucleic acid, or a polypeptide. In further embodiments, the single-stranded polynucleotide of step a) is at least 12 nucleotides in length. In still further embodiments, the single-stranded polynucleotide of step a) is at least 30 nucleotides in length. In yet further embodiments, at least one probe of step b) is at least 12 nucleotides in length. In other embodiments of the invention, at least one probe of step b) is at least 30 nucleotides in length.

Additional embodiments of the invention include a composition comprising: a) at least one target recognition agent comprising a single stranded polynucleotide; b) one or more branched polynucleotides that comprise a polynucleotide sequence partially or completely complementary to the single stranded polynucleotide of step a); and c) at least one probe comprising one or more fluorescent dyes, wherein the probe comprises a polynucleotide sequence partially or completely complementary to the one or more multistranded, branched, or dentritic polynucleotides of step b). In particular embodiments, the single-stranded polynucleotide of step a) is at least 12 nucleotides in length. In other embodiments, the single-stranded polynucleotide of step a) is at least 30 nucleotides in length. In yet other embodiments, the branched polynucleotide of step b) comprises at least two branches; at least three branches; at least four branches; at least five branches; or at least ten branches. In further embodiments of the invention, the branched polynucleotide of step b) is a dendrimer of at least 50 branches. In certain embodiments of the invention, at least one probe of step c) is at least 12 nucleotides in length. In other embodiments of the invention, at least one probe of step c) is at least 30 nucleotides in length. In yet other embodiments of the invention, the composition comprises two or more probes that each comprise a polynucleotide sequence partially or completely complementary to a branch of the branched polynucleotide of step b), wherein each probe comprises one or more different fluorescent dyes.

In certain embodiments of the invention, the probe comprises one or more fluorescent dyes selected from the group consisting of: DAPI; Hoescht 33258; FITC; Propidium Iodide; Rhodamine; Texas Red; Tetramethylrhodamine; Cyanine dyes; AlexaFluor dyes; DyLight dyes; and ATTO dyes.

BRIEF DESCRIPTION OF DRAWINGS

FIGS. 1A and 1B shows a schematic representation of specific target labeling using dynamic DNA complexes in accordance with certain embodiments of the invention.

FIG. 2A shows a schematic representation of labeling and relabeling a target with a dynamic DNA probe in accordance with certain embodiments of the invention.

FIG. 2B shows a schematic representation of labeling a target with a dynamic DNA probe and erasing and subsequently stripping said target of the probe in accordance with certain embodiments of the invention.

FIG. 3 shows the branched DNA complex of Example 1.

FIG. 4A shows fluorescent images of cells labeled with dynamic DNA complexes and GFP. FIG. 4B shows the correlation between the intensities of dynamic DNA complexes and GFP. FIG. 4C shows comparisons between theoretical and measured amplification ratios of dynamic DNA complexes.

FIG. 5A shows fluorescent images of samples labeled with dynamic DNA complexes comprising amplification ratios of 1×, 3×, and 9×. FIG. 5B shows comparisons between theoretical and measured amplification ratios of dynamic DNA complexes. FIG. 5C shows measured amplification ratios of dynamic DNA complexes compared to background.

FIG. 6 shows the use of color-time-sequence (CTS) codes for imaging a target in a sample with Stochastic Optical Reconstruction Microscopy (STORM).

DETAILED DESCRIPTION

Figure 1A:
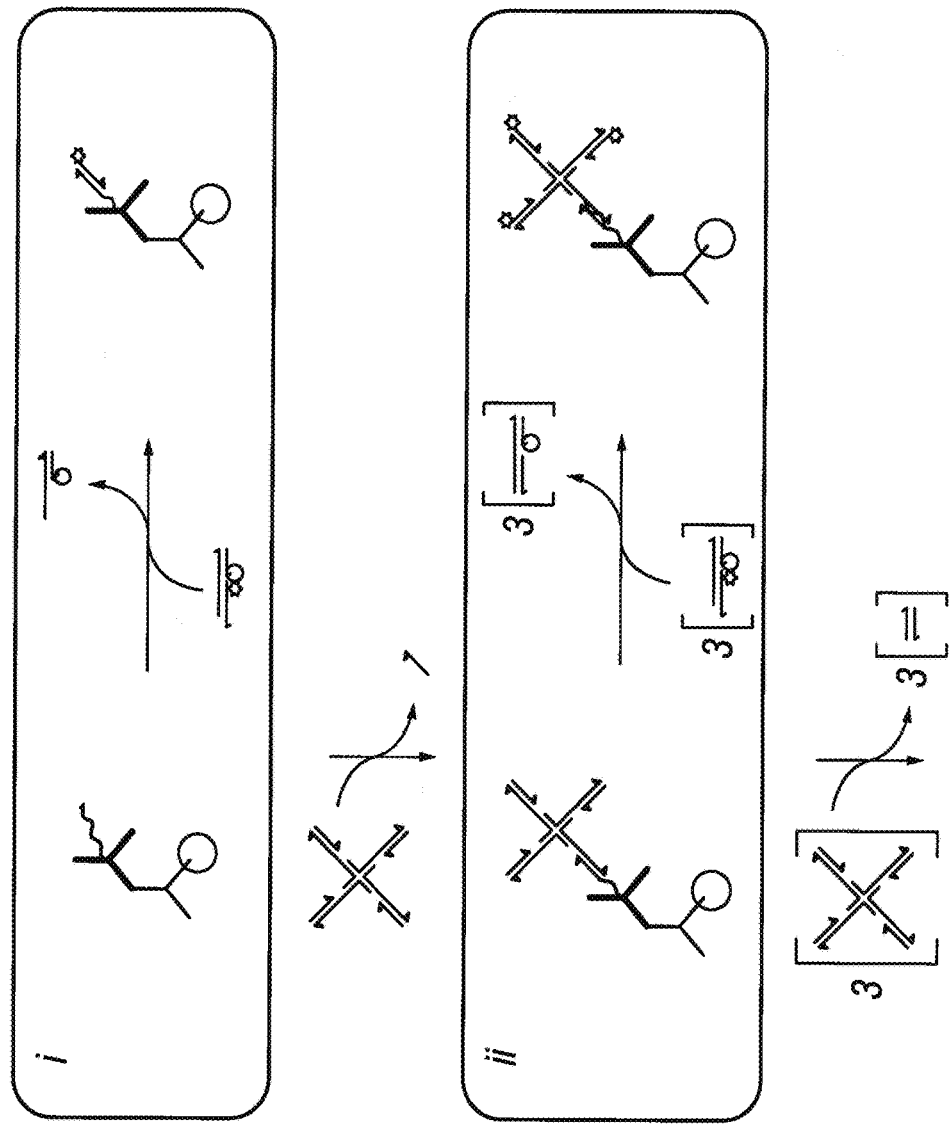
FIGS. 1A-B.

Certain embodiments of the invention relate to methods for visualizing molecular targets within a biological sample. Additional embodiments of the invention relate to methods for localization of molecular targets within a biological sample. Particular embodiments of the invention relate to methods for localization of multiple targets within a biological sample. Other embodiments of the invention provide methods for using color-time-sequence codes to identify multiple target molecules and their locations within a sample without the need to employ chemical or optical treatments (e.g., the use of denaturants) to remove targeting agents from a sample. Further embodiments of the invention may be used to controllably adapt the color and/or functionalities of a label on a particular target so that cells or tissue samples can be inspected using conventional microscopy techniques and then relabeled to facilitate highly-multiplexed molecular analyses of molecular targets, such as proteins and related biomacromolecules. While methods to strip dyes from a target are known in the art, the majority these previously known methods involve the destruction or removal of targeting agents which can perturb sample ultra-structure and integrity, thereby affecting the analysis of the sample. Other methods known in the art have focused on the sequential labeling of different molecules via less perturbative dye removal strategies. However, all of these less damaging methods implement procedures focused on the sequential labeling of different targets and imaging via conventional microscopy methods, therefore are limited by the number of dyes that can be visualized in the same sample, thereby severely limiting the number of targets that can be visualized within a single sample.

A. DEFINITIONS

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred embodiments of compositions, methods and materials are described herein. For the purposes of the present invention, the following terms are defined below.

The articles "a," "an," and "the" are used herein to refer to one or to more than one (i.e., to at least one) of the grammatical object of the article. By way of example, "an element" means one element or more than one element.

As used herein, the term "about" or "approximately" refers to a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length. In particular embodiments, the teens "about" or "approximately" when preceding a numerical value indicates the value plus or minus a range of 15%, 10%, 5%, or 1%.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

The phrase "substantially," "substantially similar," or "substantially the same", as used herein, denotes a sufficiently high degree of similarity between two numeric values or physiological outcomes, such that one of skill in the art would consider the difference between the two to be of little or no biological and/or statistical significance within the context of the biological characteristic measured. The difference between said two values is preferably less than about 20%, preferably less than about 15%, preferably less than about 10%, preferably less than about 5%, preferably less than about 2% or preferably less than about 1% as a function of the value for the reference/comparator.

Reference throughout this specification to "one embodiment," "an embodiment," "a particular embodiment," "a related embodiment," "a certain embodiment," "an additional embodiment," "an other embodiment" or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the terms "decrease" or "lower," or "lessen," or "reduce," or "abate" refers generally to the ability to produce a decrease in the quality, amount, or strength of at least one measurable quantity compared to the response caused by either vehicle or a control composition. In other particular embodiments, decreases are expressed as a fold change, such as a decrease of at least 2-fold, at least 3-fold, at least 4-fold, at least 5-fold, at least 8-fold, at least 10-fold, or even at least 15 or 20-fold, or more, relative to the vehicle or a control composition.

As used herein, the terms "retaining" or "maintaining," generally refer to the ability produce or cause a physiological response that is of a similar nature to the response caused by a vehicle or a control composition.

As used herein, the terms "promoting," "enhancing," "stimulating," or "increasing" generally refer to ability to produce an increase in one measurable quantity compared to the response caused by either vehicle or a control composition. In particular embodiments, decreases are expressed as a fold change, such as an increase of at least 2-fold, at least 3-fold, at least 4-fold, at least 5-fold, at least 8-fold, at least 10-fold, or even at least 15 or 20-fold, relative to the increase caused by either vehicle or a control composition.

As used herein, the terms "polynucleotide" or "nucleic acid" refers to RNA and DNA in any form. Polynucleotides include single and double stranded polynucleotides. Preferably, polynucleotides of the invention include polynucleotides or variants having at least about 50%, 55%, 60%, 65%, 70%, 75%, 80%, 85%, 90%, 95%, 96%, 97%, 98%, 99% or 100% sequence identity to any of the reference sequences described herein (see, e.g., Sequence Listing), typically where the variant maintains at least one biological activity of the reference sequence. In particular embodiments, the polynucleotide refers to a single stranded (ss) polynucleotide including but not limited to a ssRNA or ssDNA, e.g., oligonucleotide or aptamer. In particular embodiments, the polynucleotides are linear, branched, or dendritic.

Polynucleotides of the invention may be of any suitable length including but not limited to 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides. In particular embodiments, each polynucleotide chain of the branched or dendritic polynucleotides may be of the same or different lengths.

As used herein, the terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms include polynucleotides in which one or more nucleotides have been added or deleted, or replaced with different nucleotides compared to a reference polynucleotide. In this regard, it is well understood in the art that certain alterations inclusive of mutations, additions, deletions and substitutions can be made to a reference polynucleotide whereby the altered polynucleotide retains the biological function or activity of the reference polynucleotide.

Nucleic acids can be synthesized using protocols known in the art as described in Caruthers et al., 1992, *Methods in Enzymology* 211, 3-19; Thompson et al., International PCT Publication No. WO 99/54459; Wincott et al., 1995, *Nucleic Acids Res.* 23, 2677-2684; Wincott et al., 1997, *Methods Mol. Bio.*, 74, 59-68; Brennan et al., 1998, *Biotechnol Bioeng.*, 61, 33-45; and Brennan, U.S. Pat. No. 6,001,311).

By "nucleotide" is meant a heterocyclic nitrogenous base in N-glycosidic linkage with a phosphorylated sugar. Nucleotides are recognized in the art to include natural bases (standard), and modified bases well known in the art. Such bases are generally located at the 1" position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other (see for example, Usman and McSwiggen, supra; Eckstein et al., International PCT Publication No. WO 92/07065; Usman et al., International PCT Publication No. WO 93/15187; Uhlman & Peyman, supra). There are several examples of modified nucleic acid bases known in the art as summarized by Limbach et al., (1994, *Nucleic Acids Res.* 22, 2183-2196).

Exemplary chemically modified and other natural nucleic acid bases that can be introduced into nucleic acids, such as aptamers, for example include, inosine, purine, pyridin-4-one, pyridin-2-one, phenyl, pseudouracil, 2,4,6-trime115thoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, quesosine, 2-thiouridine, 4-thiouridine, wybutosine, wybutoxosine, 4-acetyltidine, 5-(carboxyhydroxymethyl)uridine, 5'-carboxymethylaminomethyl-2-thiouridine, 5-carboxymethylaminomethyluridine, β-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonyhnethyluridine, 5-methyloxyuridine, 5-methyl-2-thiouridine, 2-methylthio-N6-isopentenyladenosine, β-D-mannosylqueosine, uridine-5-oxyacetic acid, 2-thiocytidine, threonine derivatives and others (Burgin et al., 1996, Biochemistry, 35, 14090; Uhlman & Peyman, supra). By "modified bases" in this aspect is meant nucleotide bases other than adenine, guanine, cytosine, thymine, and uracil at 1' position or their equivalents; such bases can be used at any position, for example, within the catalytic core of an enzymatic nucleic acid molecule and/or in the substrate-binding regions of the nucleic acid molecule.

By "nucleoside" is meant a heterocyclic nitrogenous base in N-glycosidic linkage with a sugar. Nucleosides are recognized in the art to include natural bases (standard), and modified bases well known in the art. Such bases are generally located at the 1' position of a nucleoside sugar moiety. Nucleosides generally comprise a base and sugar group. The nucleosides can be unmodified or modified at the sugar, and/or base moiety, (also referred to interchangeably as nucleoside analogs, modified nucleosides, non-natural nucleosides, non-standard nucleosides and other. Exemplary chemically modified and other natural nucleic acid bases that can be introduced into nucleic acids include, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g., 6-methyluridine), propyne, quesosine, 2-thiouridine, 4-thiouridine, wybutosine, wybutoxosine, 4-acetylcytidine, 5-(carboxyhydroxymethyl)uridine, 5'-carboxymethylaminomethyl-2-thiouridine, 5-carboxymethylaminomethyluridine, β-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonylmethyluridine, 5-methyloxyuridine, 5-methyl-2-thiouridine, 2-methylthio-N6-isopentenyladenosine, β-D-mannosylqueosine, uridine-5-oxyacetic acid, 2-thiocytidine, threonine derivatives and others (Burgin et al., 1996, Biochemistry, 35, 14090-14097; Uhlman & Peyman, supra). By "modified bases" in this aspect is meant nucleoside bases other than adenine, guanine, cytosine and uracil at 1' position or their equivalents; such bases can be used at any position, for example, within the catalytic core of an enzymatic nucleic acid molecule and/or in the substrate-binding regions of the nucleic acid molecule.

As used herein the term "conjugate" in one embodiment, refers to a target recognition agent covalently or non-covalently bound to one or more polynucleotides. In another embodiment, term "conjugate" refers to a linear, branched, or dendritic polynucleotide covalently or non-covalently to one or more fluorescent dye molecules.

In various embodiments, a target recognition agent comprises an antibody or antigen binding fragment thereof, conjugated or attached to one or more single stranded polynucleotides. An "antibody" refers to a binding agent that is a polypeptide comprising at least a light chain or heavy chain immunoglobulin variable region which specifically recognizes and binds an epitope of an antigen, such as a peptide, lipid, polysaccharide, or nucleic acid containing an antigenic determinant, such as those recognized by an immune cell. Antibodies are composed of a heavy and a light chain, each of which has a variable region, termed the variable heavy (VH) region and the variable light (V 5 L) region. Together, the VH region and the VL region are responsible for binding the antigen recognized by the antibody.

An "antigen (Ag)" refers to a compound, composition, or substance that can stimulate the production of antibodies or a T cell response in an animal, including compositions (such as one that includes a tumor-specific protein) that are injected or absorbed into an animal. An antigen reacts with the products of specific humoral or cellular immunity, including those induced by heterologous antigens, such as the disclosed antigens. In particular embodiments, conjugates of the invention target (bind) antigens exposed on the cell surface of target cells. In one embodiment, the target antigen may be a polypeptide, carbohydrate, nucleic acid, lipid, hapten or other naturally occurring or synthetic compound.

An "epitope" or "antigenic determinant" refers to the region of an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. Methods of determining spatial conformation of epitopes include, for example, X-ray crystallography and nuclear magnetic resonance. Examples of antigens include, but are not limited to, peptides, lipids, polysaccharides, and nucleic acids containing antigenic determinants, such as those recognized by an immune cell. In some examples, an antigen includes a tumor-specific peptide (such as one found on the surface of a cancer cell) or immunogenic fragment thereof.

Antibodies include intact immunoglobulins and the variants and portions of antibodies well known in the art, such as Camel Ig, Ig NAR, Fab fragments, Fab' fragments, F(ab)'2 fragments, F(ab)'3 fragments, Fv, single chain Fv proteins ("scFv"), bis-scFv, (scFv)2, minibodies, diabodies, triabodies, tetrabodies, disulfide stabilized Fv proteins ("dsFv"), and single-domain antibody (sdAb, Nanobody). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Kuby, J., Immunology, 3rd Ed., W. H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE. Each heavy and light chain contains a constant region and a variable region, (the regions are also known as "domains") In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs have been defined (see, Kabat et al., *Sequences of Proteins of Immunological Interest*, U.S. Department of Health and Human Services, 1991, which is hereby incorporated by reference). The Kabat database is maintained online.

The sequences of the framework regions of different light or heavy chains are relatively conserved within a species, such as humans. The framework region of an antibody, that is the combined framework regions of the constituent light and heavy chains, serves to position and align the CDRs in three-dimensional space. The CDRs are primarily responsible for binding to an epitope of an antigen.

The CDRs of each chain are typically referred to as CDR1, CDR2, and CDR3, numbered sequentially starting from the N-terminus, and are also typically identified by the chain in which the particular CDR is located. Thus, a VH CDR3 is located in the variable domain of the heavy chain of the antibody in which it is found, whereas a VL CDR1 is the CDR1 from the variable domain of the light chain of the antibody in which it is found. Antibodies with different specificities (i.e., different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "VH" or "VH" refer to the variable region of an immunoglobulin heavy chain, including that of an Fv, scFv, dsFv or Fab. References to "VL" or "VL" refer to the variable region of an immunoglobulin light chain, including that of an Fv, scFv, dsFv or Fab.

A "monoclonal antibody" is an antibody produced by a single clone of B lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs (which generally confer antigen binding) from another species, such as a mouse.

In particular embodiments, the antibody is a humanized antibody (such as a humanized monoclonal antibody) that specifically binds to a surface protein on a cancer cell. In other embodiments, the antibody specifically binds a peptide, lipid, or carbohydrate (e.g., polysaccharide) exposed on the surface of a cancer cell or non-cancer cell, e.g., a normal cell.

A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences.

A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions, which have substantially no effect on antigen binding or other immunoglobulin functions. Humanized immunoglobulins can be constructed by means of genetic engineering (see for example, U.S. Pat. No. 5,585,089). A "human" antibody (also called a "fully human" antibody) is an antibody that includes human framework regions and all of the CDRs from a human immunoglobulin.

In one non-limiting example, the framework and the CDRs are from the same originating human heavy and/or light chain amino acid sequence. However, frameworks from one human antibody can be engineered to include CDRs from a different human antibody. All parts of a human immunoglobulin are substantially identical to corresponding parts of natural human immunoglobulin sequences.

Most cell surface protein sequences are publicly available and various other antigens can be synthesized using routine methods know to those having skill in the art. Thus, making or purchasing antibodies or other small molecules that can be used as specific binding agents for such proteins is fairly routine. In addition, novel humanized antibodies can be developed that bind cell specific target molecules.

In particular embodiments, a target recognition agent comprises a binding agent that is an antibody or antigen binding fragment thereof that binds to or recognizes a microorganism or class of microorganisms such as, for example, bacteria, fungi, protozoa, and virus. Antibodies to microorganisms and classes of microorganisms are commercially available, e.g., from Abcam, MyBioSource.com, Invitrogen, Pierce Biotechnology, Novus Biologicals, etc. Further, antibodies may be generated against any microorganism or class of microorganisms using existing methods.

In various embodiments, a target recognition agent comprises one or more aptamers. An "aptamer" may be a nucleic acid molecule, such as RNA or DNA that is capable of binding to a specific molecule with high affinity and specificity (Ellington et at, Nature 346, 818-22 (1990); and Tuerk et al., Science 249, 505-10 (1990)). Aptamers may comprise one or more modified bases, including nucleobases having one or more modified sugars and/or internucleobase linkages Aptamers are binding agents that are oligonucleic acid or peptide molecules that bind to a specific target molecule. Aptamers are usually created by selection from a large random sequence pool, but natural aptamers also exist in riboswitches. Aptamers can be used for both basic research and clinical purposes as macromolecular drugs. In particular embodiments, aptamers can be classified as: DNA or RNA or XNA aptamers that have (usually short) strands of oligonucleotides; or peptide aptamers that have a short variable peptide domain, attached at both ends to a protein scaffold.

In various embodiments, compositions and methods disclosed herein are used for imaging, classifying, or phenotyping particular target cell types. In one embodiment, the target cell is a mammalian cell. In another embodiment, the target cell is a mouse, rat, cat, dog, horse, cow, sheep, monkey, ape, or human cell.

The target cell can be a cell that is not desired or whose growth is not desired, such as a normal cell or a tumor cell. The cells can be growing in culture, or present in a mammal to be treated, such as a patient. In one embodiment, the target cell is a stem cell including, but not limited to, mesodermal stem cells, endodermal stem cells, ectodermal stem cells, mesenchymal stem cells, bone marrow stem cells, umbilical cord stem cells, placental stem cells, neural stem cells, retinal stem cells, liver stem cells, pancreatic stem cells, cardiac stem cells, kidney stem cells, and hematopoietic stem cells.

In one embodiment, the target cell is a progenitor cell including but not limited to neural progenitor cells, glial progenitor cells, retinal progenitor cells, cardiac progenitor cells, pancreatic progenitor cells, liver progenitor cells, kidney progenitor cells, and hematopoeitic progenitor cells. In one embodiment, the target cell is a pancreatic parenchymal cell, pancreatic duct cell, hepatic cell, cardiac muscle cell, skeletal muscle cell, osteoblast, skeletal myoblast, neuron, vascular endothelial cell, pigment cell, smooth muscle cell, glial cell, fat cell, bone cell, chondrocyte, pancreatic islet cell, CNS cell, PNS cell, liver cell, adipose cell, renal cell, lung cell, skin cell, ovary cell, follicular cell, epithelial cell, immune cell, or an endothelial cell.

In a particular embodiment, the target cell is a tumor cell. Exemplary tumor or cancer cells include, but are not limited to: a liquid tumor such as a leukemia, including acute leukemia (such as acute lymphocytic leukemia, acute myelocytic leukemia, and myeloblastic, promyelocytic, myelomonocytic, monocytic and erythroleukemia), chronic leukemias (such as chronic myelocytic (granulocytic) leukemia and chronic lymphocytic leukemia), polycythemia vera, lymphoma, Hodgkin's disease, non-Hodgkin's lymphoma, multiple myeloma, Waldenstrom's macroglobulinemia, heavy chain disease). In another example the cell is a solid tumor cell, such as sarcomas and carcinomas, fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, pancreatic cancer, breast cancer, ovarian cancer, prostate cancer, hepatocellular carcinoma, lung cancer, colorectal cancer, squamous cell carcinoma, basal cell carcinoma, adenocarcinoma (for example adenocarcinoma of the pancreas, colon, ovary, lung, breast, stomach, prostate, cervix, or esophagus), sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

The terms "polypeptide," "peptide," and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers.

As used herein, the term "amino acid" is intended to mean both naturally occurring and non-naturally occurring amino acids as well as amino acid analogs and mimetics. Non-naturally occurring amino acids include, for example, (D)-amino acids, norleucine, norvaline, p-fluorophenylalanine, ethionine and the like, which are known to a person skilled in the art. Amino acid analogs include modified forms of naturally and non-naturally occurring amino acids. Such modifications can include, for example, substitution or replacement of chemical groups and moieties on the amino acid or by derivitization of the amino acid. Amino acid mimetics include, for example, organic structures which exhibit functionally similar properties such as charge and charge spacing characteristic of the reference amino acid. Those skilled in the art know or can determine what structures constitute functionally equivalent amino acid analogs and amino acid mimetics.

In particular embodiments, non-naturally occurring amino acids include, without limitation, any amino acid, modified amino acid, or amino acid analogue other than selenocysteine and the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

As used herein "contacting" is defined as applying a solution containing a concentration of a specified species to a container, vessel, or sample to be analyzed. Methods of contacting may include dripping, diffusing, injecting, microfluidic application, and other methods well known to those skilled in the art.

As used herein "strand-displacement," "DNA strand-displacement," or "react via strand-displacement" or "react via DNA strand-displacement" refers to the isothermal exchange of strands between different thermodynamically stable DNA complexes.

B. TARGET RECOGNITION AGENT

In certain embodiments of the present disclosure, the target recognition agent may be, but is not limited to, an antibody such as a primary or secondary antibody, a nucleic acid such as ribonucleic acid or deoxyribonucleic acid, a peptide or oligopeptide, a nucleic acid aptamer, a peptide aptamer, an enzyme, or a self-assembling protein such as a leucine zipper, that is capable of forming a supramolecular complex with one or more molecular targets.

In particular embodiments of the invention, the target recognition agent is conjugated to a single strand of DNA (ssDNA), e.g., an oligonucleotide or DNA aptamer. In certain embodiments, the target recognition agent can be conjugated with DNA using various DNA-protein crosslinking chemistries including Click and NHS-ester-based chemistry. Recombinant antibodies can also be engineered to possess affinity tags for separately conjugated protein-DNA polymers.

C. DYNAMIC DNA COMPLEXES

In embodiments of the present disclosure, dynamic DNA complexes are polynucleotide complexes containing one or more strands of ribonucleic acid or deoxyribonucleic acid. Dynamic DNA complexes are designed to react with one another via strand displacement, the exchange of polynucleotides possessing partially or fully identical sequences between different thermodynamically stable multi-strand complexes. The reactive domains within each complex are specified so that they can react interchangeably to generate different sized DNA reporting complexes as well as to control the total number of dyes that are coupled to a molecular target.

In certain embodiments of the invention, the DNA complexes undergo three-way strand displacement, wherein a single strand of DNA reacts with a duplex strand of DNA. In further embodiments of the invention, the DNA complexes undergo four-way strand displacement, wherein the reaction occurs between two duplex strands of DNA. In certain embodiments, the duplex DNA may be multi-stranded. Three-way and four-way strand displacement reactions further are described in Duose, D. Y. Schweller, R. M. Zimak, J. Rogers, A. Hittelman, W. Diehl, M. R. (2012) "Configuring Robust DNA Strand Displacement Reactions for In Situ Molecular Analyses." *Nucleic Acids Research* 40, 3289-3298 The dynamic DNA complexes may be designed using methods known in the art. In certain embodiments of the invention, sequences of the strands contained within the dynamic DNA complexes are generated using computer-based programs, e.g., Sequin and NUPACK, that identify nucleic acid bases sequences possessing minimal sequence overlap and secondary structures and that associate with their targets with similar affinities. These techniques are described in the following references: N. Zadeh, C. D. Steenberg, J. S. Bois, B. R. Wolfe, M. B. Pierce, A. R. Khan, R. M. Dirks, N. A. Pierce. NUPACK: analysis and design of nucleic acid systems. *J Comput Chem*, 32, 170-173, 2011; R. M. Dirks, J. S. Bois, J. M. Schaeffer, E. Winfree, and N. A. Pierce. (2007) Thermodynamic analysis of interacting nucleic acid strands. *SIAM Rev*, 49, 65-88; R. M. Dirks and N. A. Pierce. (2003) A partition function algorithm for nucleic acid secondary structure including pseudoknots. *J Comput Chem*, 24, 1664-1677; R. M. Dirks and N. A. Pierce. (2004) An algorithm for computing nucleic acid base-pairing probabilities including pseudoknots. *J Comput Chem*, 25, 1295-1304; and J. N. Zadeh, B. R. Wolfe, N. A. Pierce. Nucleic acid sequence design via efficient ensemble defect optimization. *J Comput Chem*, 32, 439-452, 2011.

Without being bound by a particular theory, dynamic DNA complexes of the present invention may react using a mechanism called strand displacement: the isothermal exchange of polynucleotides (strands) between different thermodynamically stable DNA complexes. In certain embodiments of the invention, strand displacement may occur when one or more of the strands also comprises a dye, allowing this mechanism to be used to generate reporting complexes that can persist indefinitely on a sample until a reaction is performed that drives a strand exchange reaction that permutes the dye color, e.g., replacing the strand comprising the dye with another strand comprising a dye. In further embodiments, the dye bound to a target via the DNA complex may be changed via incubation procedures that are performed at ambient temperatures and without the use of chemical denaturants. Such capabilities therefore allows the color of high-affinity targeting agents (e.g., antibodies that bind their targets with >0.1 micromolar affinities) to be modulated without the use of reagents that modify dyes chemically or that employ selective bleaching treatments or methods to strip/elute targeting agents from a sample to facilitate sequential rounds of fluorescent microscopy.

In particular embodiments, strand displacement reactions are performed at an ambient temperature of at least 18° C., at least 19° C., at least 20° C., at least 21° C., at least 22° C., at least 23° C., at least 24° C., at least 25° C., at least 26° C., at least 27° C., at least 28° C., at least 29° C., at least 30° C., at least 31° C., at least 32° C., at least 33° C., at least 34° C., at least 35° C., at least 36° C., at least 37° C., at least 38° C., at least 39° C., or at least 40° C. In certain embodiments, the incubation procedures are performed at an ambient temperature of about 18° C. to about 19° C., about 19° C. to about 20° C., about 20° C. to about 21° C., about 21° C. to about 22° C., about 22° C. to about 23° C., about 23° C. to about 24° C., about 24° C. to about 25° C., about 25° C. to about 26° C., about 26° C. to about 27° C., about 27° C. to about 28° C., about 28° C. to about 29° C., about 29° C. to about 30° C., about 30° C. to about 31° C., about 31° C. to about 32° C., about 32° C. to about 33° C., about 33° C. to about 34° C., about 34° C. to about 35° C., about 35° C. to about 36° C., about 36° C. to about 37° C., about 37° C. to about 38° C., about 38° C. to about 39° C., about 39° C. to about 40° C., or about 40° C. to about 41° C.

In certain embodiments, strand displacement reactions are performed at an ambient temperature in a mild buffer including, but not limited to phosphate buffered saline, ringer's solution, or TRIS.

In certain embodiments of the invention, the dynamic DNA complexes are designed to be used interchangeably both to generate structurally-organized, branched or dendritic reporting complexes that possess different number of terminal branches and to control the number of dye molecules coupled to each branch. As seen in FIG. 1, dynamic DNA complexes allow for the self-assembly of organized immunofluorescent reporting complexes. In a particular embodiment of the invention, a target protein is detected, quantified, or bound to a primary antibody (Ab) and a DNA-conjugated secondary antibody conjugated or covalently bound to a ssDNA tag. In particular embodiments, strand displacement reactions are then performed to label the ssDNA tag directly with one or more linear, DNA probe complexes, e.g., 1, 2, 3, 4, or 5, wherein each probe complex carries between 1 and 3 dye molecules (FIG. 1*i*), or to build branched dynamic DNA complexes to increase the number of target sites for the linear probe's displacement reactions (FIGS. 1ii and 1iii). One of skill would understand that the dynamic DNA complexes illustrated in FIG. 1 represent only certain illustrative embodiments of the present invention and are not intended to limit the invention to these classes of compounds.

In certain embodiments, dynamic DNA complexes of the present invention include, but are not limited to, complexes with at least 1, at least 2, at least 3, at least 4, at least 5, at least 6, at least 7, at least 8, at least 9, or at least 10 dye molecules present, and each complex being linear or having one, two, three, four, or five or more branches, and/or dendritic complexes.

Again with reference to FIG. 1, dynamic DNA complexes self-assemble into labeling complexes via strand displacement. In certain embodiments of the invention, labeling complexes comprise three modular components: a ssDNA-conjugated target recognition agent (such as the DNA-Ab conjugate of FIG. 1) to facilitate target recognition; at least one multi-stranded, branched, or dendritic DNA complexes that add additional DNA appendages to the ssDNA-conjugated target recognition agent; and linear, labeling DNA complexes that label each terminal branch of a complex with at least one dye molecule.

Dynamic DNA complexes are designed to optimally react with one another via strand displacement. The reactive domains within each complex are specified so that they can react interchangeably to generate different sized DNA reporting complexes and to control the total number of dyes that are coupled to their molecular target.

In particular embodiments of the invention, a dynamic DNA complex may have 3 to 50 branches, including all ranges and subranges therebetween; e.g., 3 to 5 branches, 3 to 9 branches, 3 to 15 branches, 3 to 18 branches, 3 to 25 branches, 3 to 40 branches, 5 to 9 branches, 5 to 15 branches, 5 to 18 branches, 5 to 20 branches, 5 to 25 branches, 5 to 40 branches, 5 to 50 branches, 8 to 10 branches, 8 to 12 branches, 8 to 15 branches, 8 to 20 branches, 10 to 15 branches, 10 to 20 branches, 10 to 30 branches, 10 to 40 branches, 10 to 50 branches, 25 to 40 branches, 25 to 50 branches, an 40 to 50 branches. In further embodiments of the invention, the dynamic DNA complex is a multi-generation dynamic DNA complex wherein a branched or dendritic structure has undergone at least one further strand displacement reaction such that another branched or dendritic structure has been added to at least one of the terminal branches of the original dynamic DNA complex.

In certain embodiments of the invention, the dynamic DNA complex comprises "covering strands". Covering strands are polynucleotide sequences which are complexed to the terminal end of a branched or dendritic dynamic DNA complex and are displaced in subsequent strand displacement reactions.

In certain embodiments of the invention, the dynamic DNA complexes further comprise a toe-hold domain, a small, single-stranded domain of about 2-15 nucleotides (nt), which partially hybridizes to the target to accelerate the initiation rates of the strand displacement reaction. In particular embodiments of the invention, the toe-hold domain is 3 nt, 4 nt, 5 nt, 6 nt, 7 nt, 8 nt, 9 nt, 10 nt, 11 nt, 12 nt, 13 nt, 14 nt, or 15 nt.

Dynamic DNA probes, or probes, are dynamic DNA complexes further comprising a suitable dye. In certain embodiments of the invention, the dynamic DNA probe is a single DNA strand. In further embodiments, the dynamic DNA probe is a DNA duplex. In particular embodiments of the invention dynamic DNA probes comprise multi-stranded dynamic DNA complexes. In further embodiments of the invention, a multi-stranded dynamic DNA probe comprises two strands. In still further embodiments of the invention, a multi-stranded dynamic DNA probe comprises three strands. In particular embodiments of the invention, the dynamic DNA probe further comprises quencher.

Figure 1B:
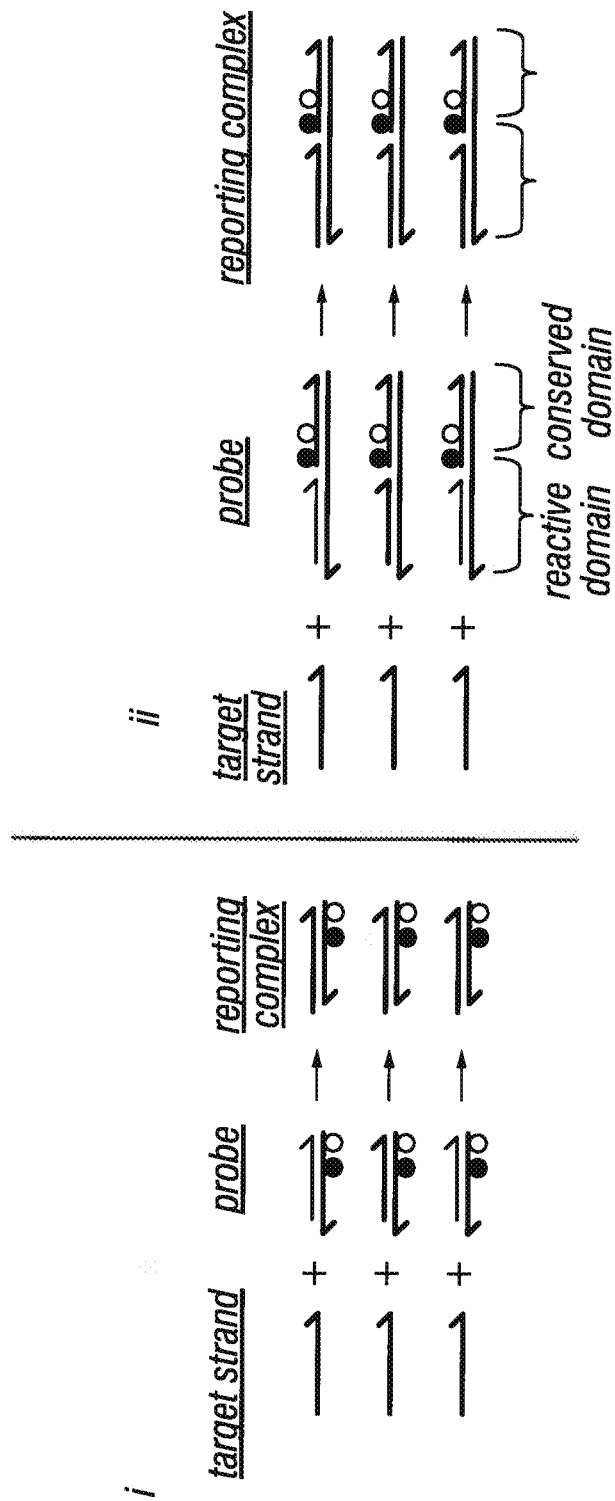

In particular embodiments of the invention, the probe is a DNA duplex comprising two strands, wherein the reactive domain and the dye are on the same strand (see FIG. 1Bi). In further embodiments, the probe is a DNA duplex comprising at least three strands, wherein the reactive domain and the dye-carrying domain are distinct. In certain embodiments of the invention, wherein the reactive domain and the dye-carrying domain are distinct, the dye-carrying domain may be used with several different reactive domains, thereby avoiding the need to separately label a reactive domain for each target (see FIG. 1Bii).

In certain embodiments of the invention, a duplex or multi-strand dynamic DNA probe is prepared prior to any strand displacement or labeling steps using standard hybridization procedures known in the art.

The dye or quencher can be conjugated to the dynamic DNA complex using any suitable method known in the art. In particular embodiments, a dye or quencher is incorporated into a probe using specific domains. In certain embodiments of the invention, the dye or quencher comprises a functional group that allows for incorporation into the nucleic acid strand. In still further embodiments, the dye or quencher is a modified nucleic acid base.

Any dye suitable for use in a biological sample may be used in the present invention. In particular embodiments of the invention, suitable dyes for use include, but are not limited to: DAPI; Hoescht 33258; FITC; Propidium Iodide; Rhodamine; Texas Red; Tetramethylrhodamine; Cyanine dyes (e.g., Cy2, Cy3; Cy3B, Cy3.5, Cy5; Cy5.5; Cy7); AlexaFluor dyes (e.g., Alexa Fluor 350, Alexa Fluor 405, Alexa Fluor 430, Alexa Fluor 488, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700, Alexa Fluor 750, and Alexa Fluor 790); DyLight dyes (e.g., DyLight 350, DyLight 405, DyLight 488, DyLight 550, DyLight 594, DyLight 633, DyLight 650, DyLight 680, DyLight 755, and DyLight 800); and ATTO dyes (e.g., ATTO 390, ATTO 425, ATTO 465, ATTO 488, ATTO 495, ATTO 520, ATTO 532, ATTO 550, ATTO 565, ATTO 590, ATTO 594, ATTO 610, ATTO 611X, ATTO 620, ATTO 633, ATTO 635, ATTO 637, ATTO 647, ATTO 647N, ATTO 655, ATTO 665, ATTO 680, ATTO 700, ATTO 725, ATTO 740).

In particular embodiments of the invention, the probe is labeled with two different dyes suitable for use in techniques requiring photoswitching or photoactivating, such as Stochastic Optical Reconstruction Microscopy (STORM). Such dye pairs include those in which the emitter undergoes blinking, or fluorescence intermittency. Suitable dyes include, but are not limited to: Cy2 and Alexa Fluor 647; Cy 3 and Alexa Fluor 647; Cy2 and Cy 7; Cy3 and Cy5; Cy 3 and Cy 5.5; Cy3 and Cy 7; Alexa Fluor 405 and Alexa Fluor 647; Alexa Fluor 405 and Alexa Fluor 488; Alexa Fluor 405 and Alexa Fluor 555; Alexa Fluor 488 and Cy 7; Alexa Fluor 488 and Alexa Fluor 647.

Figure 3:
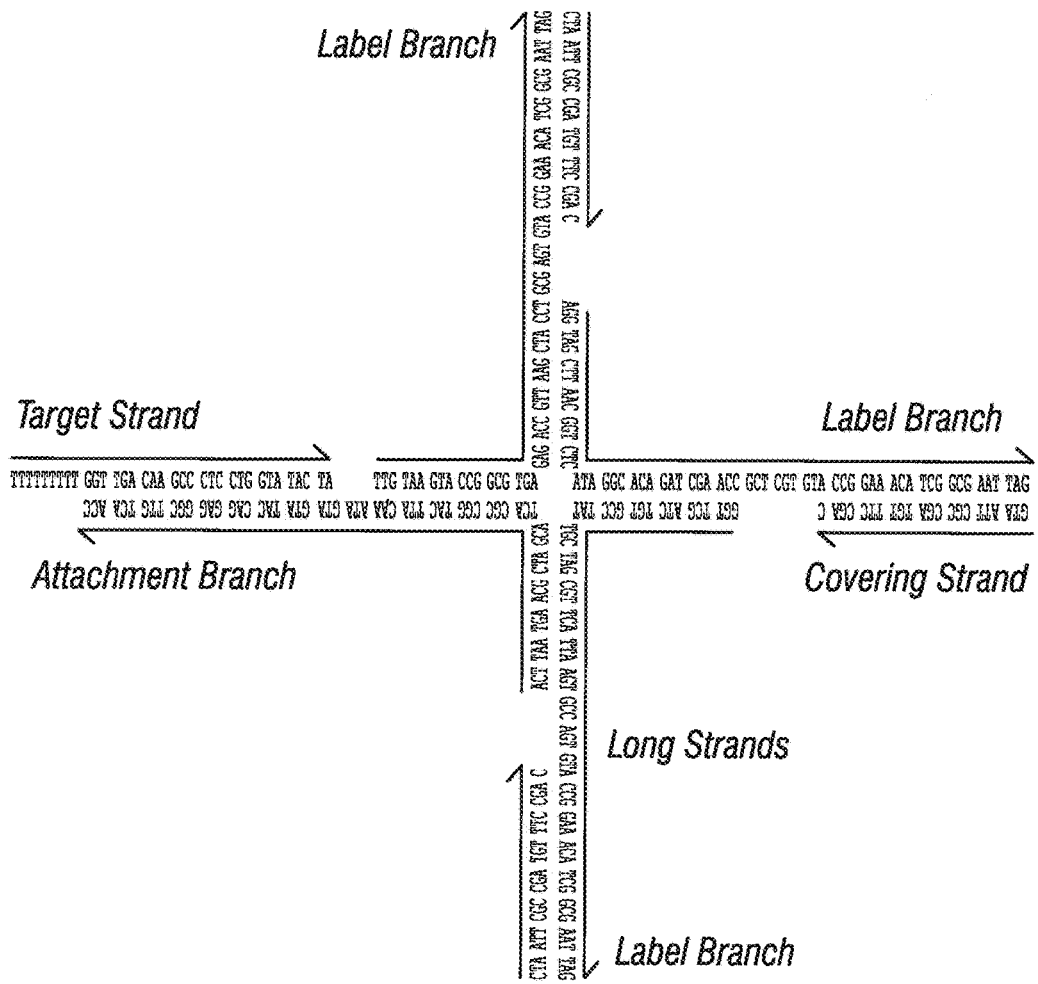
FIG. 3.

In certain embodiments of the invention a dynamic DNA complex can be displaced from a labeling complex via an "eraser" strand. Without being bound by any particular mechanism, the eraser strand and labeling complex undergo a strand displacement reaction and the dynamic DNA complex is stripped from the DNA-conjugated target complex (see FIG. 3B). In particular embodiments, an eraser strand is used to strip a dynamic DNA probe from a labeling complex. In further embodiments, the stripped DNA-conjugated target complex is subsequently relabeled with another dynamic DNA probe. In certain embodiments, the eraser is a single stranded polynucleotide and undergoes three-way strand displacement with a labeling complex. In other embodiments, the eraser is a double stranded polynucleotide and undergoes four-way strand displacement with a labeling complex.

D. REPRESENTATIVE CONDITIONS FOR STRAND DISPLACEMENT REACTIONS

In certain embodiments of the invention, strand displacement occurs at ambient temperatures. In further embodiments of the invention, strand displacement occurs at room temperature. In still further embodiments of the invention, strand displacement occurs between about 4° C. to about 37° C. including all ranges and subranges there between, e.g., about 4° C. to about 10° C.; about 4° C. to about 20° C.; about 4° C. to about 25° C. about 10° C. to about 20° C.; about 10° C. to about 25° C.; about 10° C. to about 37° C.; about 18° C. to about 22° C.; 18° C. to about 32° C., about 20° C. to about 26° C., about 20° C. to about 37° C.; about 22° C. to about 28° C., about 22° C. to about 37° C., about 23° C. to about 27° C., about 24° C. to about 30° C., about 26° C. to about 32° C., about 28° C. to about 32° C. In yet further embodiments, strand displacement takes place at about 4° C. In other embodiments, strand displacement takes place at about 30° C. In certain embodiments, strand displacement takes place at about 37° C.

In further embodiments of the invention, strand displacement occurs in any suitable buffer known in the art. In still further embodiments, the buffer is a mild, non-denaturing buffer. In particular embodiments, the buffer is phosphate buffered saline (PBS) or a tris buffer, such as TAE (tris base/acetic acid/EDTA) or TBE (tris base/boric acid/EDTA). In certain embodiments of the invention, the buffer comprises additional components, such as Buffer BB (Qiagen), $Mg^{2+}$, BSA, herring sperm DNA, salmon sperm DNA, calf thymus DNA, polyT DNA, dextan sulfate, or mixtures thereof. In further embodiments of the invention, strand displacement takes place in 1×TAE buffer with 12.5 mM $Mg^{2+}$. In still further embodiments of the invention, strand displacement takes place in 1×TAE buffer with 12.5 mM $Mg^{2+}$ and 10% Buffer BB. In yet further embodiments of the invention, strand displacement takes place in 1×TAE buffer with 12.5 mM $Mg^{2+}$; 1% BSA; 5 mg/ml herring sperm DNA, salmon sperm DNA, or calf thymus DNA; 0.5 µM polyT DNA; and 1% dextan sulfate.

In certain embodiments of the invention, the polynucleotide strands are present at concentration of about 5 nM to about 500 µM, including all ranges and subranges therebetween, e.g. about 5 nM to about 10 nM, about 5 nM to about 50 nM, about 5 nM to about 100 nM, about 5 nM to about 250 nM, about 5 nM to about 500 nM, about 10 nM to about 25 nM, about 10 nM to about 50 nM, about 10 nM to about 100 nM, about 10 nM to about 250 nM, about 10 nM to about 500 nM, about 10 nM to about 1 µM, about 25 nM to about 50 nM, about 25 nM to about 100 nM, about 25 nM to about 250 nM, about 25 nM to about 500 nM, about 25 nM to about 1 µM, about 25 nM to about 2 µM, about 50 nM to about 100 nM, about 50 nM to about 250 nM, about 50 nM to about 500 nM; about 50 nM to about 1 µM; about 50 nM to about 10 µM; about 50 nM to about 50 µM; about 100 to about 250 nM; about 100 nM to about 500 nM; about 100 nM to about 1 µM; about 100 nM to about 10 µM; about 100 nM to about 50 µM; about 100 nM to about 500 µM; about 250 nM to about 500 nM; about 250 nM to about 1 µM; about 250 nM to about 10 µM; about 250 nM to about 50 µM; about 250 nM to about 500 µM; about 500 nM to about 1 µM; about 500 nM to about 5 µM; about 500 nM to about 10 µM; about 500 nM to about 25 µM; about 500 nM to about 50 µM; about 100 nM to about 500 µM; about 1 µM to about 5 µM; about 1 µM to about 10 µM; about 1 µM to about 25 µM; about 1 µM to about 40 µM; about 1 µM to about 50 µM; about 1 µM to about 100 µM; about 1 µM to about 250 µM; about 1 µM to about 500 µM; about 5 µM to about 10 µM; about 5 µM to about 25 µM; about 5 µM to about 40 µM; about 5 µM to about 50 µM; about 5 µM to about 100 µM; about 5 µM to about 250 µM; about 5 µM to about 500 µM; about 10 µM to about 25 µM; about 10 µM to about 40 µM; about 10 µM to about 50 µM; about 10 µM to about 75 µM; about 10 µM to about 100 µM; about 10 µM to about 250 µM; about 10 µM to about 500 µM; about 25 µM to about 50 µM; about 25 µM to about 75 µM; about 25 µM to about 100 µM; about 25 µM to about 250 µM; about 25 µM to about 500 µM; about 50 µM to about 100 µM; about 50 µM to about 250 µM; about 50 µM to about 500 µM; about 100 µM to about 250 µM; about 100 µM to about 500 µM; and about 250 µM to about 500 µM.

In further embodiments of the invention, the strand displacement reaction is performed for about 5 minutes to about 12 hours, including all ranges and subranges therebetween; e.g.; about 5 minutes to about 15 minutes; about 5 minutes to about 30 minutes; about 5 minutes to about 45 minutes; about 5 minutes to about 60 minutes; about 15 minutes to about 30 minutes; about 15 minutes to about 45 minutes; about 15 minutes to about 60 minutes; about 15 minutes to about 90 minutes; about 30 minutes to about 60 minutes; about 30 minutes to about 90 minutes; about 30 minutes to about 2 hours; about 45 minutes to about 60 minutes; about 45 minutes to about 90 minutes; about 45 minutes to about 2 hours; about 45 minutes to about 2.5 hours; about 1 hour to about 1.5 hours; about 1 hour to about 2 hours; about 1 hour to about 3 hours; about 1 hour to about 4 hours; about 1 hour to about 5 hours; about 1 hour to about 8 hours; about 1 hour to about 12 hours; about 1.5 hours to about 2 hours; about 1.5 hours to about 3 hours; about 1.5 hours to about 5 hours; about 1.5 hours to about 8 hours; about 2 hours to about 3 hours; about 2 hours to about 5 hours; about 2 hours to about 8 hours; about 2 hours to about 12 hours; about 3 hours to about 5 hours; about 3 hours to about 8 hours; about 5 hours to about 8 hours; and about 5 hours to about 12 hours.

In particular embodiments of the invention, strand displacement reactions take place in TBE, at about 23° C. to about 27° C., for about 1 to about 5 hours, with 100 µM to 500 µM concentration of the dynamic DNA complex.

In certain embodiments of the reaction, when undergoing sequential stand displacement reactions, a sample may be washed by any suitable buffer, including, but not limited to PBS, TAE, and TBE. In particular embodiments, the sample is washed at about 20° C. to about 30° C. In other embodiments, the sample is washed at room temperature. In still other embodiments, the sample is washed at about 4° C. In further embodiments, the sample is washed one to three times. In still further embodiments, the sample is washed for 30 minutes to 12 hours.

In particular embodiments of the invention, a branched or dendritic dynamic DNA complex is prepared via strand displacement prior to exposure to the sample using techniques known in the art (see D. Y. Duose, R. M. Schweller, J. Zimak, A. R. Rogers, W. N. Hittelman, M. R. Diehl, Nucleic Acids Res. 2011, 1-10; D. Y. Duose, R. M. Schweller, W. N. Hittelman, M. R. Diehl, Bioconj. Chem. 2010, 21, 2327-2331; and X. Wang, N. C. Seeman, J. Am. Chem. Soc. 2007, 129, 8169-8176. In further embodiments of the invention, a branched or dendritic dynamic DNA complex is prepared via strand displacement and purified prior to exposure to the sample. In still further embodiments of the invention, a branched or dendritic dynamic DNA complex is purified by any suitable method known in the art, including, but not limited to size exclusion chromatography, fast protein liquid chromatography (FPLC), high-performance liquid chromatography (HPLC), gel electrophoresis, polyacrylamide gel electrophoresis (PAGE), and combinations thereof.

In certain embodiments of the invention, samples are prepared for labeling by dynamic DNA complexes by any suitable method known in the art. In further embodiments, the samples may be fixed using any suitable method known in the art. In still further embodiments, cells are seeded onto a suitable substrate, such as glass coverslips, and grown to the desired confluency prior to fixation. In particular embodiments of the invention, samples, such as cells or tissues, are blocked prior to labeling to prevent non-specific adhesion.

E. TUNING LABELING COLOR AND INTENSITIES THROUGH DYNAMIC DNA COMPLEXES

In particular embodiments of the invention, a molecular target may be labeled with one or more dye molecules via strand displacement reactions with dynamic DNA complexes. In further embodiments of the invention, a molecular target may be labeled with one, two, three, four, five, six, seven, eight, nine, or ten or more molecules of the same dye via strand displacement reactions with dynamic DNA complexes. In still further embodiments of the invention, a molecular target may be labeled with two, three, four, five, six, seven, eight, nine, or ten or more or more different dyes via strand displacement reactions with dynamic DNA complexes. In yet further embodiments, a molecular target may be labeled with more than one molecule of two, three, four, five, six, seven, eight, nine, or ten or more different dyes via strand displacement reactions with dynamic DNA complexes. In certain embodiments of the invention, the strand displacement reactions take place as described above.

In certain embodiments, labeling intensities can be varied in a single stage strand displacement reaction between a polynucleotide-conjugated target recognition agent and a linear dynamic DNA probe that carries different numbers of dyes. In other embodiments, the number of labeling sites per polynucleotide-conjugated target recognition agent can be increased via sequential strand displacement reactions that produce single or multi-generational branched or dendritic DNA complexes whose terminal branches can be labeled in subsequent reactions with a dynamic DNA probe (FIGS. 1ii and 1iii).

In certain embodiments of the invention, dynamic DNA complexes can be used to generate structurally-organized, branched or dendritic reporting complexes that possess different number of terminal branches, e.g., 2, 3, 4, 5, 6, 7, 8, 9, 10, or dendrimers, as described above. In further embodiments of the invention, dynamic DNA complexes can be used to control the number of dye molecules coupled to each branch.

In particular embodiments of the invention, the number of dye molecules used to label a target may be modulated via one or more strand displacement reactions with dynamic DNA complexes in order to control the reporting intensities of labeled targets.

Further embodiments of the invention allow for the reporting intensity of a labeled target to be modulated. In certain embodiments, a target in a sample may be labeled with a first dynamic DNA complex carrying one or more dye molecules In certain embodiments of the invention, a cell or tissue sample is contacted with a target-recognition agent comprising a polynucleotide such that the target is complexed with the target-recognition agent to form a polynucleotide-target complex, which is then reacted via strand displacement with a branched or dendritic dynamic DNA complex to create a dynamic-DNA target complex, which is then reacted, via strand displacement, with a first probe comprising at least one dye and a polynucleotide to form a labeling complex. In particular embodiments of the invention, the branched or dendritic dynamic DNA complex has a polynucleotide sequence partially or completely complementary to the polynucleotide complexed to the target. In further embodiments the dye is a fluorescent dye and the cell or tissue sample visualized with any suitable microscopy technique in order to determine the location of the target.

In further embodiments of the invention, a cell or tissue sample is contacted with a target-recognition agent comprising a polynucleotide such that the target is complexed with the target-recognition agent to form a polynucleotide-target complex, which is then reacted via strand displacement with a branched or dendritic dynamic DNA complex to create a dynamic-DNA target complex, which is then further reacted via strand displacement with additional branched or dendritic dynamic DNA complexes to create a multi-generation dynamic DNA-target complex. In certain embodiments, the terminal branches of a multi-generation dynamic DNA-target complex are then labeled via strand displacement with a probe comprising a polynucleotide and at least one dye. In particular embodiments of the invention, the branched or dendritic dynamic DNA complex has a polynucleotide sequence partially or completely complementary to the polynucleotide of the probe. In additional embodiments of the invention, the number of strand displacement reactions, the number of branches, and the number of dyes of dynamic DNA-target complex can be expressed using the notation: P(# displacement reactions, # branches, # dyes). For example, the largest reporting complex in FIG. 1(iii), which is formed through 3 three displacement reactions, has 9 branches and a single dye on each branch, is designated as P(3,9,9).

Figure 2:
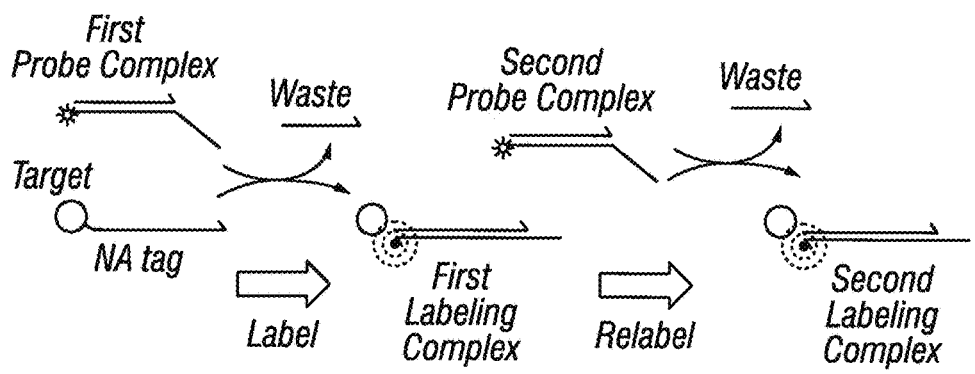
FIG. 2.
Figure 2:
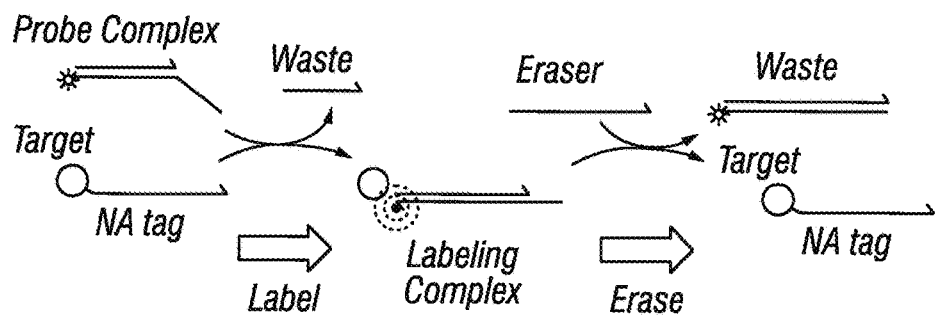

In particular embodiments of the invention, a labeled target can be relabeled with a second dynamic DNA probe that may comprise a different type of dye and/or a different number of dye molecules that the first dynamic DNA probe used to label the target. In further embodiments of the invention, the sample is contacted with a second probe comprising at least one dye and a polynucleotide which, via strand displacement, displaces the first probe from the labeling complex to form a second labeling complex. (see FIG. 2A) In still further embodiments of the invention, the sample is contacted with a polynucleotide which, via strand displacement removes the first probe from the labeling complex and subsequently contacted with a second probe comprising at least one dye and a polynucleotide which, via strand displacement, reacts with the polynucleotide-target complex to form a second labeling complex. (see FIG. 2B) The polynucleotide-target complex is shown in FIGS. 2A and 2B as a linear complex for simplicity, however it is to be understood that in certain embodiments of the invention, the polynucleotide-target complex may be a branched, dendritic and/or multi-generation dynamic DNA complex. The probe shown in FIGS. 2A and 2B is shown as a two-stranded, singly labeled polynucleotide for simplicity, however it is to be understood that any suitable probe describe herein may be used for labeling and/or relabeling. In particular embodiments of the invention the probe comprises at least two dye molecules. In other embodiments of the invention, the probe is a single strand polynucleotide. In still other embodiments of the invention, the probe is a multi-strand polynucleotide. In yet further embodiments of the invention, the sample is washed between these steps.

In particular embodiments of the invention, the target can be relabeled as described above more than once. In certain embodiments of the invention, the target can be relabeled as described above up to ten times. In further embodiments of the invention, the target can be relabeled as described above up to eight times. In still further embodiments of the invention, the target can be relabeled as describe above up to five times. In still further embodiments of the invention, the target can be relabeled as describe above up to three times.

In particular embodiments of the invention, the probe may comprise more than one dye. In certain embodiments of the invention, the probe may comprise one to five dyes. In further embodiments of the invention, the probe may comprise more than two different types of dyes. In still further embodiments of the invention, the probe may comprise activator and imaging dye pairs suitable for Stochastic Optical Reconstruction Microscopy (STORM). In certain embodiments of the invention, the target recognition agent is an antibody such as a primary or secondary antibody, a nucleic acid such as ribonucleic acid or deoxyribonucleic acid, a peptide or oligopeptide, a nucleic acid aptamer, a peptide aptamer, an enzyme. In further embodiments of the invention, target recognition occurs through a primary antibody and a nucleic acid-conjugated secondary antibody.

The invention also provides methods for tuning the reporting intensities of labeled targets via strand displacement reactions with dynamic DNA complexes. In certain embodiments, a target in a sample may be labeled with a first dynamic DNA complex and probe carrying one or more dye molecules as described above, the sample imaged, and based on the measured reporting intensity versus the preferred reporting intensity, the target may be relabeled, as described above, with a second dynamic DNA complex and/or second probe, carrying one or more dye molecules to form a second labeling complex, wherein the second probe carries a different number and/or type of dye molecules based on the difference between the measured reporting intensity and the desired reporting intensity. In a particular embodiment, the first labeling complex and the second labeling complex have a 36:1 to 1:36 to ratio of dye molecules. In further embodiments of the invention, the first labeling complex and the second labeling complex have a 9:1 to 1:9 ratio of dye molecules.

In certain embodiments of the invention, a branched or dendritic dynamic DNA complex may be used to amplify the labeling intensity of a dilute target in a sample. In particular embodiments, a dilute target complexed with a target-recognition agent comprising a polynucleotide to form a polynucleotide-target complex; the polynucleotide-target complex is then reacted via strand displacement with a branched or dendritic dynamic DNA complex comprising 2 to 11 branches to create a dynamic-DNA target complex, which is then reacted with a dynamic DNA probe via strand displacement such that the dynamic DNA probe labels each branch of the branched or dendritic dynamic DNA complex. In certain embodiments, each dynamic DNA probe comprises 1 to 3 dye molecules, resulting in 2× to 33× amplification of the signal than if the target had been labeled directly with a single dye. In further embodiments, a dilute target complexed with a target-recognition agent comprising a polynucleotide to form a polynucleotide-target complex; the polynucleotide-target complex is then reacted via strand displacement with a first branched or dendritic dynamic DNA complex comprising 2 to 5 branches to create a dynamic-DNA target complex, which is then reacted with a second branched or dendritic dynamic DNA complex comprising 2 to 5 branches via strand displacement such that each branch of the first branched or dendritic dynamic DNA complex is further complexed with a second branched or dendritic dynamic DNA complex to create a multi-generation dynamic DNA complex with 4 to 25 branches. The multi-generation dynamic DNA complex is then is then reacted with a dynamic DNA probe via strand displacement such that the dynamic DNA probe labels each branch of the complex. In certain embodiments, each dynamic DNA probe comprises 1 to 3 dye molecules, resulting in 4× to 75× amplification of the signal than if the target had been labeled directly with a single dye.

In certain embodiments of the invention, the labeling intensity of a dilute target can be amplified with branched or dendritic dynamic DNA complexes in order to provide ordered and quantifiable amplification such that the reporting signal of a dilute target is not influenced by the noise generated by spatially and spectrally overlapping signals from more abundant targets.

In further embodiments of the invention, a target labeled with a dynamic DNA complex may be stripped of the dynamic DNA complex via strand displacement reactions. In still further embodiments of the invention, a target labeled with a first dynamic DNA complex may be stripped of the dynamic DNA complex via strand displacement reactions and relabeled with a second dynamic DNA complex via strand displacement reactions. In yet further embodiments of the invention, a target labeled with a first dynamic DNA complex may be stripped of the dynamic DNA and relabeled with a second dynamic DNA complex via strand displacement reactions.

F. COLOR-TIME-SEQUENCE (CTS)

The invention also provides methods for identifying the locations of various molecular targets in a sample by repeated labeling and imaging of molecular targets with multiple dyes in a predetermined order to provide each target with a distinctive color-time-sequence (CTS) code that may be used to identify the target by determining the combination of colors, or dyes, that co-localize in a merged image of the sample and the time-sequence that they appeared. In particular embodiments of the invention, the present invention is directed to methods to visualize many different molecular targets within a biological sample including but not limited to 2, 3, 4, 5, 6, 7, 8, 9, 10, 20, 30, 40, 50, 60, 70, 80, 90, or 100 or more targets.

Certain embodiments of the present invention allow for the visualization and localization of many more targets (e.g., proteins, and other biomarkers) in the same sample than current state of the art optical microscopy methods permit. In particular embodiments of the invention, the CTS method provides non-linear scaling of the number of distinct molecular targets that can be visualized within the same location of a sample (e.g., the same cell or tissue section).

In particular embodiments of the invention, DNA-conjugated recognition agents can be used to label different targets within a sample with different DNA tags. Via strand displacement reactions as described above, dynamic DNA probes (dynamic DNA complexes comprising at least one dye and at least one polynucleotide) are used to label each DNA-tag according to a programmed code that is designated for each target. The initial dynamic DNA probes are then removed, and a second round of labeling occurs. In particular embodiments of the invention, the probe has a polynucleotide sequence partially or completely complementary to the DNA tag conjugated to the target recognition agent. In certain embodiments of the invention, the removal of one dynamic DNA probe from the complex and the addition of another dynamic DNA probe occur in the same step. In still other embodiments, the dye is modulated, rather than dynamic DNA probes removed. Samples are imaged after each round of labeling and the CTS code for each target is determined by observing the co-clustering of single-molecule detection events within sequential images of the sample that are collected for each round. In certain embodiments of the invention, samples may be imaged by any suitable technique capable of determining the location, or centroid position, of a single molecule. In particular embodiments of the invention, any suitable single molecule localization microscopy-based super resolution imaging technology may be used, such as, but not limited to STORM.

The code is based on the order of the dyes, and therefore, assuming that each target is labeled with a single dye in each round, the number of targets that can be visualized scales polynomially with the number of labeling/imaging rounds: (# probe colors)$^{[\# \text{ of rounds}]}$, (.e.g, 3-color, 2-stage imaging could be used to detect 9 separate targets as shown in Table 1, 6-color, 2-stage imaging could be used to detect 36 separate targets). The ability to program the association of multiple dyes (number, type, geometric arrangement) simultaneously with molecular targeting agents provides a chemical route to increase the code complexity in order to enhance this scaling and to integrate code elements that can facilitate the discrimination of errors in the identification of spectral identity of dye molecules.

TABLE 1

Example of CTS codes for nine targets using two-rounds of three-color imaging with red (R), blue (B), and green (G) dyes.

| Target | Round 1 | Round 2 |
|--------|---------|---------|
| 1 | Red | Red |
| 2 | Red | Blue |
| 3 | Red | Green |
| 4 | Blue | Red |
| 5 | Blue | Blue |
| 6 | Blue | Green |
| 7 | Green | Red |
| 8 | Green | Blue |
| 9 | Green | Green |

In other embodiments of the invention, each target is labeled with one two, three, four, five, six, seven, eight, nine, or ten or more dyes. In a particular embodiment of the invention, each target of interest in a sample may undergo the following labeling and imaging steps: complexing a target-specific recognition agent with the target, wherein the target-specific recognition agent comprises a polynucleotide with a sequence unique to the target to form a polynucleotide-target complex; reacting the polynucleotide target complex with a first dynamic DNA probe to form a first labeling complex, and visualizing the sample via any suitable microscopy technique in order to determine the location of the dye-labeled target on a single molecule level. The first dynamic DNA probe is replaced, via strand displacement, with a second dynamic DNA probe to form a second labeling complex, and again the sample is visualized in order to determine the location of the dye-labeled target.

In particular embodiments of the invention, the CTS method provides for the use of dynamic DNA complexes to change the color of target recognition agents such antibodies and other protein recognition technologies (e.g., aptamers and engineered peptides) after they have been bound to their targets within a cell or tissue sample. In particular embodiments of the invention, these steps comprise: 1) synthesizing DNA-conjugated forms of these targeting agents, 2) binding the DNA-conjugated targeting agents to their targets within cells, and 3) performing a series of chemical reactions using engineered, dynamic DNA complexes that are designed to either a) label each reagent with dye molecules, b) strip the strand bearing the dye from their target, or c) replace the dyes on a target with new dye molecules. The latter two steps of stripping one dye and replacing it with another may be performed separately or combined into a single incubation step in the CTS procedure.

In further embodiments of the invention, the DNA complexes may also contain one or more domains that allow the DNA complex to carry and label their target with one or more dyes. In still further embodiments of the invention, quencher molecules, which can remove and/or change the dye colors, may be incorporated into the DNA complexes. In yet further embodiments of the invention, the quencher molecules may be used to reduce background signals produced by non-specifically adhered DNA complexes bearing dye molecules.

In particular embodiments of the invention, the strand displacement reaction is a three-way strand displacement reaction. In other embodiments of the invention, the strand displacement reaction is a four-way strand displacement reaction.

In particular embodiments, samples undergo more than one additional round of labeling and imaging. In certain embodiments of the invention, samples undergo two to ten rounds of labeling and imaging. In further embodiments of the invention, samples undergo two to eight rounds of labeling and imaging. In further embodiments of the invention, samples undergo three to six rounds of labeling and imaging.

In certain embodiments of the invention, the target recognition agent is an antibody such as a primary or secondary antibody, a nucleic acid such as ribonucleic acid or deoxyribonucleic acid, a peptide or oligopeptide, a nucleic acid aptamer, a peptide aptamer, an enzyme. In further embodiments of the invention, target recognition occurs through a primary antibody and a nucleic acid-conjugated secondary antibody.

In other embodiments of the invention, each target is labeled with more than one dye each round, providing an even greater number of unique CTS codes that can be used to distinguish targets in the same sample. In still other embodiments of the invention, each target is labeled with two to five different dyes each round.

Certain embodiments of the invention provide methods to avoid the photobleaching of a labeled target. Photobleaching of dyes or fluorophores may impair detection techniques, as photobleaching may complicate the observation of fluorescent molecules, since they will eventually be destroyed by the light exposure necessary to stimulate them into fluorescing. This can be particularly problematic in time-lapse microscopy. In certain embodiments of the present invention, the strand displacement methods described herein can be used to replenish bleached fluorophores within a sample, which may improve the fidelity of super-resolution imaging methods.

Any microscopy technique that is capable of detecting and localizing single fluorophores within a sample may be used with any of the embodiments of the invention. A sample may first be imaged using standard imaging techniques that do not provide single-molecule detection capabilities, and then subsequently imaged using any of the embodiments described herein, such as the CTS method. This approach allows users to define regions of interest within a sample that can then be selected for highly multiplexed CTS analyses.

In further embodiments of the invention, the CTS method may involve the modulation of a target recognition agent's (e.g., an antibody) color and can be employed for multiplexed imaging using super-resolution microscopy or conventional microscopy approaches. Examples of super-resolution imaging procedures that are compatible with CTS include, but are not limited to: ground state depletion and individual molecule return (GSDIM), stochastic optical reconstruction microscopy (STORM) methods including direct STORM (dSTORM), and stimulated emission depletion methods (STED). In further embodiments of the invention, CTS can be configured to allow a variety of conventional microscopy methods, including but not limited to, confocal and wide-field imaging techniques.

The development of CTS for super-resolution imaging methods may provide a simple route to increase the number of molecular targets that can be visualized simultaneously in a single cell using these methods without compromising on their high spatial resolution. The use of CTS with conventional, snap-shot, microscopy techniques may provide a method to profile the states of many proteins within a large biological sample by allowing multiple images of the same sample to be collected more rapidly.

Both the super-resolution and conventional-microscopy forms of CTS may utilize dynamic imaging probe technologies that integrate DNA-conjugated target recognition agents (e.g., DNA-conjugated antibodies, DNA aptamers), and dynamic DNA complexes to controllably change or modulate the label of a target within a sample.

It is also within the scope of this disclosure that the entire CTS procedure and its variations may be performed manually or through automated control systems that introduce actuated exchange fluids containing the dyes.

In particular embodiments of the invention, the use of CTS to label and localize molecular targets provides improved multiplexed marker level delineation over conventional in situ imaging procedures. In other embodiments of the invention, the use of CTS to label and localize molecular targets provides the user with the ability to label and localize a significantly greater number of targets than allowed by current in situ imaging procedures.

The above attributes are uniquely useful for protein detection since spatial barcodes, whether generated using conventional or super-resolution imaging approaches, cannot be generated for proteins without procedures to synthesis structured polymers that are connected to a protein. While the present invention provides a unique route to create reporting complexes possessing these properties, it also allows sequential codes to be generated using such structures or small DNA tags on a sample. This ability is ultimately important since it provides abilities generate color-time-codes without compromising the resolution of an imaging approach. There is also the advantage of a smaller label size, which means the ultimate # of proteins that can be labeled is higher compared to methods employing spatial barcodes.

Another advantage of certain embodiments of the present invention is that the methods employ techniques to generate stable reporting complexes where the reporting dye molecules are coupled tightly to their target. The CTS approach is distinct from methods where weak binding reagents (e.g., the use of short DNA tags that reversibly bind their targets in DNA-Paint procedures) are used to detect molecules since probes can be labeled under saturating conditions, and hence, buffering conditions and environmental factors will influence labeling less significantly. Fewer parameters must be optimized using CTS in order regulate dye labeling. Moreover, CTS can be adapted specifically for super-resolution/localization microscopies that employ optical methods to control dye reporting rates and probabilities, whereas, DNA-paint does not offer this option. Uses for certain embodiments of the invention Regulation of Probe Reporting Performance and Code Complexity Via Multi-Strand, Branched, and/or Dendritic DNA Complexes In certain embodiments of the present invention, multi-strand, branched, and/or dendritic DNA complexes may be used to regulate the number of dyes, the type of dyes, the combinations of dyes types, and the spatial arrangements of the dyes within a reporting complex that is coupled to a molecular recognition agent/molecular target. In particular embodiments of the invention, such control may be achieved via strand displacement between combinations of linear multi-strand, branched, and/or dendritic dynamic DNA complexes. Such DNA complexes may be outfitted with dye molecules in order to self-assemble reporting complexes on a target via sequential strand displacement reactions. Strand displacement may also be used to regulate reporting intensities within a sample by providing a way to controllably tune the dye labeling levels. Such complexes may be used, for example, to improve existing multiplexed imaging methods that rely on standard microscopy techniques or spectral deconvolution methods by providing a simple route to balance dye levels on a sample. These multi-strand, branched and/or dendritic DNA complexes may also be used to increase the complexity of the color codes for each target in the CTS procedure (e.g., by allowing combinations of different dyes to be coupled to molecular targeting agents in a controlled stoichiometry). In certain embodiments of the invention, multi-strand, branched, and/or dendritic DNA complexes may allow larger numbers targets to be stained and visualized simultaneously in a single microscopy round of CTS compared to the base version that employs 1:1 dye:target labeling in a round.

FIG. 1 provides an illustration describing a particular embodiment of the invention wherein via strand displacement, dynamic DNA complexes form immuno-targeted reporting complexes. In a certain embodiment of the invention, fluorescent reporting complexes are generated using three different modular components: a ssDNA-conjugated antibody to facilitate protein recognition, multi-stranded and branched DNA complexes that are used to add additional DNA appendages to the antibody-conjugate, and a linear probe complex that is used to outfit the individual appendages or branches with fluorescent dye molecules. The branched and linear probe complexes both possess domains that allow them to react with one another via analogous strand displacement processes. Reporting complexes are assembled via sequential displacement reactions that couple either linear probes or branched complexes to the antibodies. In further embodiments of the invention, antibody intensities can be varied in a single stage reaction by labeling them with linear probes that carry different numbers of dyes, e.g., one, two, three, four, five, six, seven, eight, nine, or ten or more dyes. In still further embodiments of the invention, single or multiple branched complexes can be coupled to the antibodies to increase the number of sites that can be labeled in subsequent reactions with the labeling probe.

Controlled Amplification for Balancing the Intensity of Labeling in Conventional Microscopy Images In further embodiments of the invention, the ability to couple controlled numbers of fluorophores to individual targets, such as antibodies, in a multiplexed fashion may be advantageous for in situ molecular analyses. This method allows for the improvement target detection sensitivities without compromising abilities to quantitate target levels in a sample. The dynamic, branched complexes may facilitate more direct comparative analyses of target levels across different biological samples (e.g., cell samples or tissue sections) since the amplification reactions will converge on a pre-determined and programmed value (i.e., a preset number of dyes per antibody). These methods of the present invention may have advantages over existing technologies including rolling circle amplifications, and tyramide signal amplification (TSA) that rely on chemical reactions that are divergent (i.e., they produce labeling levels that depend on the time over which a reaction is performed and yield variable amplification levels within a sample.

In certain embodiments of the invention, a branched or dendritic dynamic DNA complex may be used as described above to amplify the labeling intensity of a dilute target in a sample. In some embodiments, a target is complexed to single branched or dendritic dynamic DNA complex. In other embodiments, at target is complexed to a multi-generational dynamic DNA complex. These branched, dendritic, or multi-generational DNA complexes can then undergo a strand displacement reaction with a dynamic DNA probe comprising 1 to 3 dye molecules. The sample can then be imaged to identify particular Regions of Interest (ROIs) and the dynamic DNA probes erased as described above. In particular embodiments of the invention, the ROIs are further analyzed using any of the CTS procedures described above.

The ability to regulate amplification levels may also offer an important route to balance labeling intensities for conventional multiplexed imaging analyses. Such control is important to hyperspectral imaging procedures requiring the use of spectral deconvolution algorithms to deconvolve signal emanating from overlapping fluorescent dye molecules within a sample. The dynamic range of a detector is implicitly split between labels or dyes that overlap spectrally. Thus, the presence of a bright label or dye in a sample can inhibit the detection of other labels or dyes that are less intense. The ability to set label or dye intensities at fixed targeting-agent/dye labeling ratios provides a route to adjust labeling intensities to minimize these types of issues. Moreover, individual branches of the reporting complexes formed after amplification reactions can also be labeled with the same or different-color fluorescent probes, allowing their identity to be further distinguished by specifying stoichiometric color combinations. The branched complexes can also be disassembled to facilitate multiple measurements on the same sample. Such control could be used to perform multiple immunofluorescence analyses on the same sample or to switch between imaging modalities (e.g., from standard immunofluorescence imaging via epi-fluorescence or confocal microscopy or other low resolution techniques to super-resolution imaging methods.

Improved 3-Dimensional Spatial Resolution Via Site Triangulation

In further embodiments of the invention, the branched DNA probes may be designed such that the geometric presentation of each branch relative to a targeting agent's recognition site (e.g., the variable antigen recognition domain of a DNA conjugated antibody) is known and controlled. The combination of the projection of the branches in a single image plane, and the localization of the dyes on each branch may be used to triangulate the actual position of the portion of the target (e.g. the protein epitope) recognized by the targeting agent. This capability provides a route to increase the 3-dimensional resolution of super-resolution procedures since localization is now performed via a combination of three measurements in the x-y plane of an image in addition to 3 measurements in the z-plane of the microscope (which will serve to average out noise in individual measurements of the dye positions on each branch). Of note, axial resolution enhancements will be appreciable using this adaptation of the invention since x-y localization accuracies are higher than axial localization accuracies.

Switching Imaging Modalities from Conventional Labeling to CTS

In certain embodiments of the invention, a microscopy user switch between conventional and super-resolution imaging procedures. For example, select targets may be labeled to specifically facilitate imaging via conventional epi-fluorescence or confocal microscopy techniques. in further embodiments of the invention, hyperspectral imaging procedures may also be employed. In each case, the ability to regulate the number of dyes coupled to individual targets can be used to balance labeling levels appropriately in order to minimize spectral crosstalk or bleed-through of emmision spectra across a microscope's spectral channels. The dyes labeling these targets can then be replaced with dyes that are suitable for super-resolution microscopy-based CTS (e.g., pairs of dye molecules that are arranged spatially on a DNA duplex to facilitate STORM super-resolution imaging procedures).

In a particular embodiment of the invention, targets may be labeled with dyes using branched dynamic DNA complexes and imaged using confocal hyperspectral imaging methods. The number of branches in a complex and the number of dye molecules coupled to each branch may be controlled to tune the levels of each dye in order to optimize the use of linear spectral deconvolution of dye signals that are necessary to separate signals within a sample. These dye-bearing complexes on the targets and/or the dynamic DNA complexes, may then be replaced with probes possessing individual dye molecules or combinations of dye molecules that are suitable for super-resolution microscopy (e.g., activator and imaging dye pairs employed for STORM). In certain embodiments of the invention, targets that were not labeled and/or imaged by the first method may be labeled using additional DNA complexes comprising appropriate dyes, such as STORM probes, to facilitate a super-resolution microscopy-based CTS imaging of user-defined set of targets.

In certain embodiments of the invention, super-resolution CTS may also be implemented to switch between super-resolution imaging methods without the need to employ harsh chemicals or dye bleaching procedures to remove dyes from a sample. In further embodiments of the invention, a sample could be imaged using the traditional multi-dye STORM procedure, and then dSTORM using singly labeled probes. In still further embodiments of the invention, the switching between methods may be integrated at part of CTS. In yet further embodiments of the invention, these methods could be added as separate step to integrate targeting agents that are not labeled with DNA.

Highly Multiplexed Protein Immunofluorescence

In certain embodiments of the invention, the number of distinct targets that may be detected within a single cell may be enhanced greatly using color coded super-resolution microscopy as compared to traditional, direct super-resolution imaging methods. The number of targets that may be visualized simultaneously increases dramatically as the number of different color probes increases and scales polynomially with the number of times that a sample is labeled. Such abilities may greatly enhance existing molecular analyses of cells and tissues and be used to gain more detailed molecular understandings of cellular states in diseases.

Improved Delineation of Specific and Non-Specific Antibody Recognition

In further embodiments of the invention, the ability to multiplex in situ single molecule detection may allow for the discrimination of specific and non-specific protein detection events by employing multiple antibodies that target different epitopes on the same protein target. Selective recognition events may then be discriminated from non-specific binding of antibodies by examining antibodies that co-localize on the same target.

Multiplexed In Situ Detection of Total and Post-Translationally Modified Proteins In further embodiments of the invention, the coding of single molecule antibody localizations may be combined with other protein-epitope recognition reagents that may detect post-translationally modified protein residues. In a particular embodiment, protein specific antibodies are employed to identify different proteins within a sample via direct or coded super-resolution imaging. Additional recognition agents that recognize post-translational modifications of epitopes on the same protein may then used to determine which individual antibodies imaged within a sample co-localize with signals (single molecule localizations) generated by these reagents. In certain embodiments of the invention, these recognition agents may be phosphospecific antibodies, other small molecules, peptides, or protein domains that bind modified amino acid residues. Moreover, these protein binders may have high or low affinity for their target. High affinity recognition agents may be labeled with DNA to facilitate CTS. In further embodiments of the invention, a sample can be analyzed by CTS, the probes and dyes removed, and low affinity probes may be used. For example, low affinity recognition reagents may be used to image amino acid modifications via a super-resolution imaging procedure based on the transites localization of probes upon their binding to a target (a version of a method called points accumulation for imaging in nanoscale topography, PAINT). By examining the co-localization of these recognition agents to the position of proteins imaged via the first round of dynamic DNA-based CTS, one may delineate whether a protein of interest possess one of these modifications, or whether a protein that associates closely with a target is modified. The development of substrate-dependent targeting reagents that bind to modified residues on specific peptide sequences would allow for analyses of multiple post-translational modification samples via this imaging combination without the need to generate antibodies for each protein target.

Optimization of Probe Activation Deactivation Responses

In further embodiments of the invention, dynamic DNA complexes may incorporate dedicated domains that may be custom tailored to optimize the number and spatial orientation of the fluorophore reporters for each antibody. Such control may be harnessed to optimize probe intensities and switching responses in order to maximize the ratio that a probe reports specifically/non-specifically. Probe responses may be regulated by controlling the relative positions of or distances between fluorophores within a dynamic DNA complex. In still further embodiments, one, two, three, four, five, six, seven, eight, nine, or ten or more dyes may be incorporated into these domains to gain such control, and further expand upon the diversity of the single molecule color code.

EXAMPLES

The following examples show various embodiments of the invention. The examples are for illustration purposes only and are not intended to limit the scope of the disclosure.

Example 1

Branched Dynamic DNA Probe Construction

DNA complex sequences were designed on a per-domain basis using a MATLAB script that generates and concatenates domains based on multiple criteria, including two-state hybridization energies, melting temperatures, strand concentrations, and salt concentrations as described in Duose et. al, Nucleic Acids Res. 2011, 1-10 and Duose et al, Bioconj. Chem. 2010, 21. 2327-2331. Representative sequences can be found in Table 2.

TABLE 2

List of oligonucleotide sequences used in design of DNA probe complexes. /5Hexynyl/, /5Cy5/, /5Cy3/, /5AlexaFluor488/, /3IAbRQSp/, /3IABkFQ/ indicate a 5' hexynyl, Cy5, Cy3, AlexaFluor488, 3' Iowa Black re quencher, or Iowa Black green quencher modification, respectively.

| Amine Strands | | SEQ ID NO: |
|---|---|---|
| PS3 I & PS4 I /5AmMC6/ | TTTTTTTTTGG CCA CCG AGA CAA TAC GCA GGA CCC | 1 |
| PS1 I & PS2 I /5AmMC6/ | TTTTTTTTTGT GTA CCG GAA ACA TCG GCG AAT TAG | 2 |
| PS5 I & PS6 I /5AmMC6/ | TTTTTTTTTTT ACG CGG TAC ACC TGT GCG GAT ATA | 3 |

TABLE 2-continued

List of oligonucleotide sequences used in design of DNA probe complexes. /5Hexynyl/, /5Cy5/, /5Cy3/, /5AlexaFluor488/, /3IAbRQSp/, /3IABkFQ/ indicate a 5' hexynyl, Cy5, Cy3, AlexaFluor488, 3' Iowa Black re quencher, or Iowa Black green quencher modification, respectively.

| | Amine Strands | SEQ ID NO: |
|---|---|---|
| | Hexynyl Strands | |
| PS3 I & PS4 I | /5Hexynyl/ TTTTTTTTTGG CCA CCG AGA CAA TAC GCA GGA CCC | 4 |
| PS1 I & PS2 I | /5Hexynyl/ TTTTTTTTTGT GTA CCG GAA ACA TCG GCG AAT TAG | 5 |
| PS5 I & PS6 I | /5Hexynyl/ TTTTTTTTTTT ACG CGG TAC ACC TGT GCG GAT ATA | 6 |
| PS3 & PS4 BC1 | Long Strands | |
| BC1-1 | ACT TAA TGA ACG CTA GCA TCA CGC CGG TAC TTA CAA GGT ATA GTA TAC CAG GAG GGC TTG TCA ACC | 7 |
| BC1-2 | TTG TAA GTA CCG GCG TGA GAG ACC GTT AAG CTA CCT GCG AGT GTA CCG GAA ACA TCG GCG AAT TAG | 8 |
| BC 1-3 | AGG TAG CTT AAC GGT CTC ATA GGC ACA GAT CGA ACC GCT CGT GTA CCG GAA ACA TCG GCG AAT TAG | 9 |
| BC1-4 | GGT TCG ATC TGT GCC TAT TGC TAG CGT TCA TTA AGT GCC AGT GTA CCG GAA ACA TCG GCG AAT TAG | 10 |
| | Covering Strands | |
| BC1-5 | AAG GTA TAG TAT ACC AGG AGG GCT TGT C | 11 |
| BC1-6 | AAA AAA AAT TCG CCG ATG TTT CCG AC | 12 |
| PS5 & PS6 BC2 | Long Strands | |
| BC2-1 | CAC TGT TCA CTT CAC GCT TTG GTC GCT TCC ACG AAC GAG CAT CCA TGT GAG GGC GCT TAT TGT ATT CAG AGA | 13 |
| BC2-2 | GTT CGT GGA AGC GAC CAA TAC TCG TTT CAC CGT CAA CCT GCG GTC TGG CGA ATG TAG CGT ATG TGC TC | 14 |
| BC2-3 | TTG ACG GTG AAA CGA GTA ATT GAC GTA TGC TGG TTC CGA GAG GTC TGG CGA ATG TAG CGT ATG TGC TC | 15 |
| BC2-4 | GAA CCA GCA TAC GTC AAT AGC GTG AAG TGA ACA GTG AAT GTC TGG CGA ATG TAG CGT ATG TGC TC | 16 |
| | Covering Strands | |
| BC2-5 | CAA ATA CAA TAA GCG CCC TCG TGC AA | 17 |
| BC2-6 | GTA TGA GCA CAT ACG CTA CAT TCG TT | 18 |
| PS5 & PS6 BC3 | Long Strands | |
| BC3-1 | GAA TCC GAG AAG GTC GAA TCG CAC GAC ATT CCG GTG ATT TGG ACG CAG GCA CAT ACG CTA CAT TCG CCA GAC | 19 |
| BC3-2 | CAC CGG AAT GTC GTG CGA GCG AGA AAT CAC AGC ATA CGC GTT TTA CGC GGT ACA CCT GTG CGG ATA TA | 20 |
| BC3-3 | TAT GCT GTG ATT TCT CGC TGA CAC CAA GGC AAC CAT GAT CTA TTA CGC GGT ACA CCT GTG CGG ATA TA | 21 |
| BC3-4 | ATG GTT GCC TTG GTG TCA TTC GAC CTT CTC GGA TTC GTT TAG TTA CGC GGT ACA CCT GTG CGG ATA TA | 22 |
| | Covering Strands | |
| BC3-5 | AAC GAA TGT AGC GTA TGT GCT CAT AC | 23 |
| BC3-6 | AAA AAA AAA TAT CCG CAC AGG TGT ACC AT | 24 |
| Dye Complex Strands | | |
| FQ | CGT AAT AGC GCT AGT CTC/3IABkFQ/ | 25 |
| PS1 & PS3 D | /5Cy3/TTTCTT GTC AAT TCG CCG ATG TTT CCG TA CAC | 26 |
| PS1 & PS3 L | GT CGG AAA CAT CGG CGA ATT TTT TTT GAG ACT AGC GCT ATT ACG | 27 |
| PS2 & PS4 D | /5Cy3/TTTCTT GTC AAT TCG CCG ATG TTT CCG GTA CAC/3Cy3Sp/ | 28 |
| PS2 & PS4 L | /5Cy3/GT CGG AAA CAT CGG CGA ATT TTT TTT GAG ACT AGC GCT ATT ACG | 29 |
| PS5 D | /5Cy3/TTT CAA ACG TAT CCG CAC AGG TGT ACC GCG TAA | 30 |
| PS5 L | AT GGT ACA CCT GTG CGG ATA TTT TTT TTT TTT GAG ACT AGC GCT ATT ACG | 31 |
| PS6 D | 5-/5Cy3/TTT CAA ACG TAT CCG CAC AGG TGT ACC GCG TAA /3Cy3Sp/ | 32 |
| PS6 L | AT GGT ACA CCT GTG CGG ATA TTT TTT TTT TTT GAG ACT AGC GCT ATT ACG | 33 |

Each complex was prepared by thermally annealing its strands in solution prior to use in labeling protocols. The branched DNA complexes were annealed using a method described in X. Wang. N. C. Seeman, J. Am. Chem. Soc.

2007. 129. 8169-8176. The four covering strands (C) and four long (L) strands in these complexes were mixed in 1×TAE buffer with 12.5 mM $Mg^{2+}$ in a 5:4 (L:C) stoichiometric ratio. The strands were heated to 95° C. for two min and then transferred to a 2 L water bath at 95° C. The water bath was then put in a polystyrene insulated container and cooled to 4° C. over two days. The branched DNA complexes were purified using size exclusion chromatography. After the annealing reaction, the product was purified at 4° C. by FPLC using a Superdex 200 10/300 GL column and a PBS flow rate of 250 µL/min. The relevant fractions containing branched complexes were then concentrated by butanol extraction and ethanol precipitation, followed by drying on a centrafugal evaporator. The resultant structures (see FIG. 3) were then examined by 7% non-denaturing PAGE analyses using SYBRGold staining (Invitrogen).

Example 2

In Situ Demonstration of Complex Assembly

HeLa cells exogenously expressing a GFP-leucine zipper construct (GFP-$Z_E$) were exposed to an artificial protein polymer, $Z_R$-ELS$_6$-ssDNA that associates tightly with the $Z_E$ tag.

The number of dyes per the GFP-$Z_E$ target was modulated by either labeling the ssDNA-tags directly with a linear probe that comprises a single Cy3 dye, or by coupling a single or multiple branched DNA complexes of Example 1 to the $Z_R$-ELS$_6$-ssDNA polymers in sequential displacement reactions as shown in FIG. 1iii, and then labeling the terminal sites of the DNA complexes using a linear probe that comprises a single Cy3 dye.

Figure 4A:
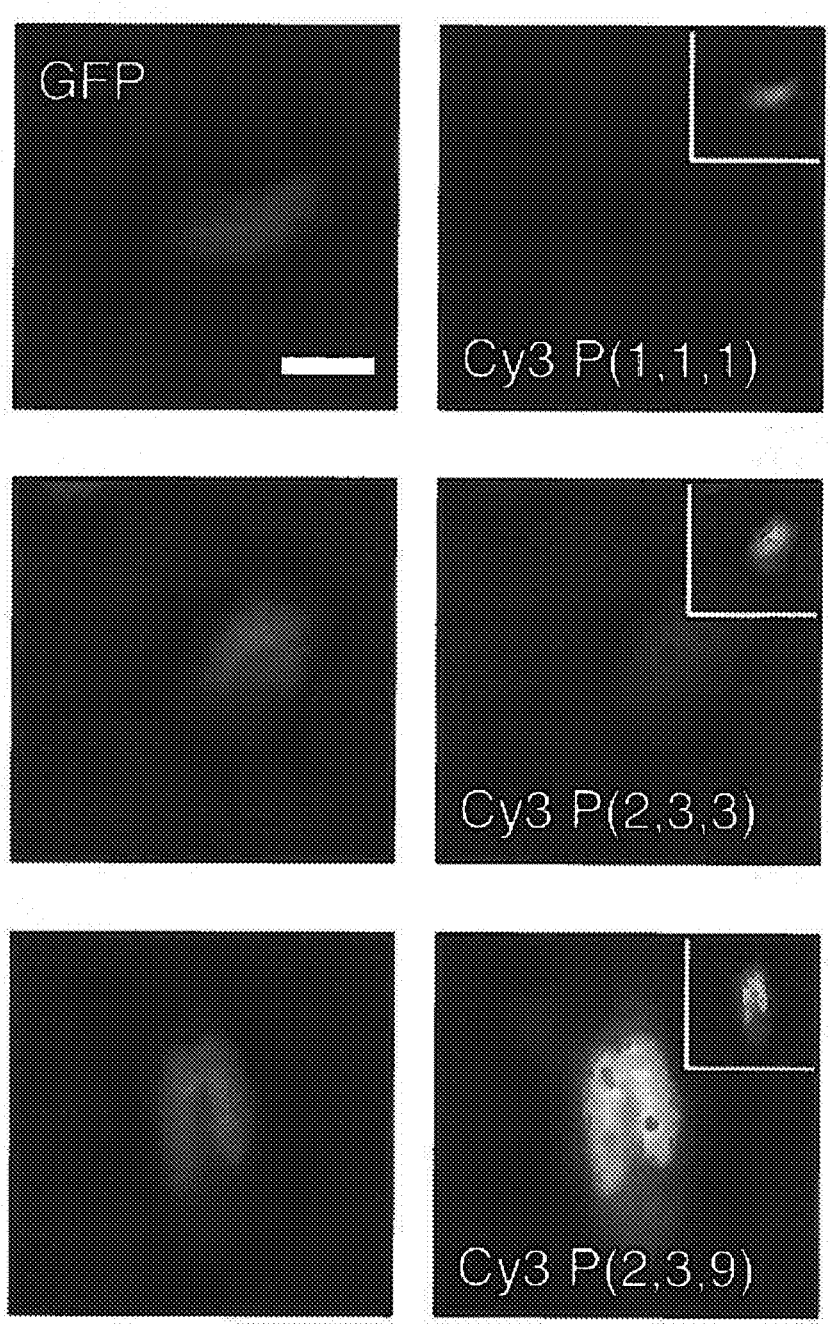
FIGS. 4A-C.

Representative fluorescent images of these labeled cells are shown in FIG. 4A, with the channel reporting the GFP intensity on the left and the channel reporting the Cy3 intensity on the right. The expected number of reactions required to build a structure and the number branches and dyes per GFP protein are indicated using the notation: P(# displacement reactions, # branches, # dyes). For example, the largest reporting complex in FIG. 1 (iii), which is formed through 3 displacement reactions, has 9 branches and a single dye on each branch, is designated as P(3,9,9).

Figure 4B:
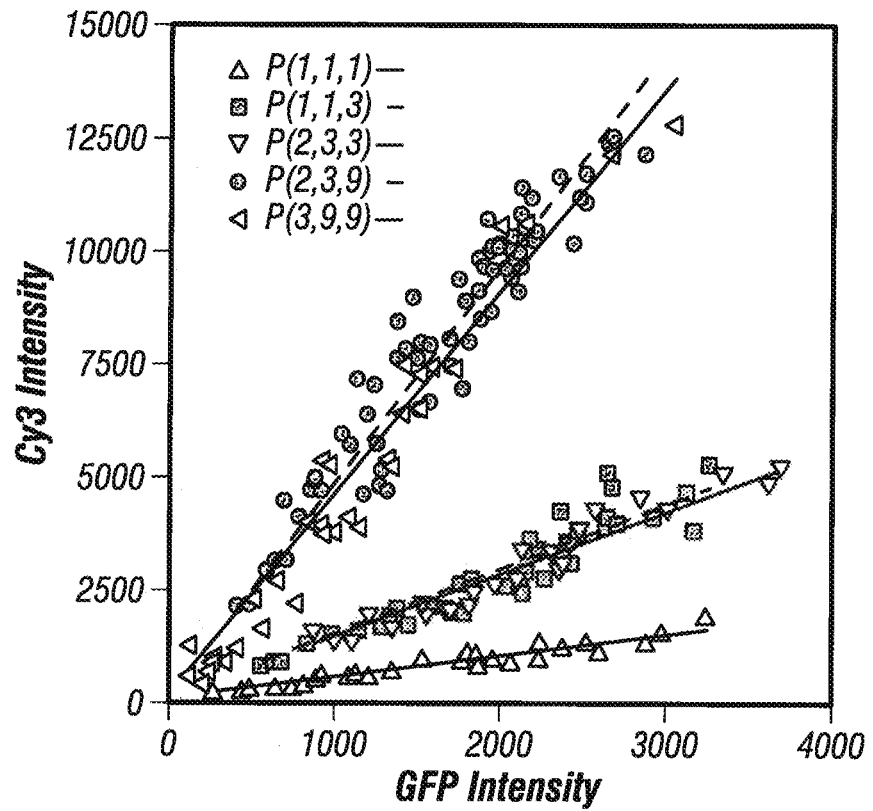

FIG. 4B shows the correlations between average DNA-probe and GFP intensities. Each plot shows the average intensities of the cytoplasmic regions of 30 cells.

Figure 4C:
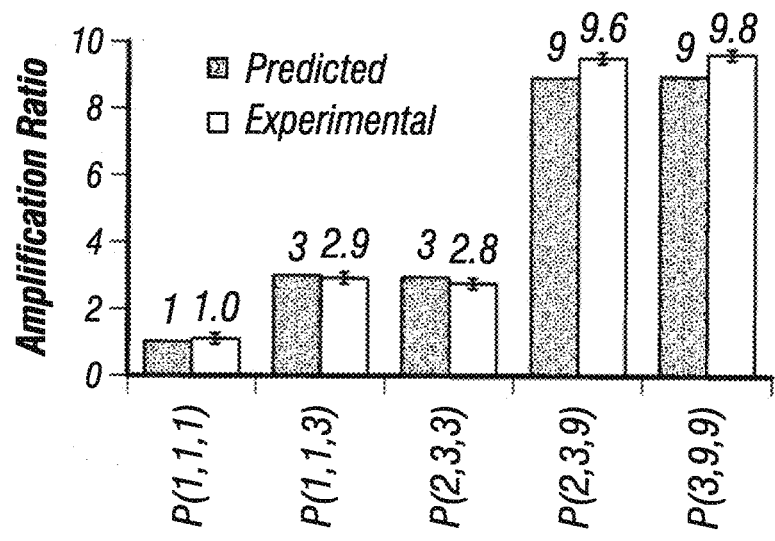

FIG. 4C shows comparisons of theoretical and measured amplification ratios for the reporting complexes analyzed FIG. 4B. Theoretical amplification ratios indicate the maximum number of dyes that can be integrated into a complex. Experimental ratios are determined by dividing the slopes from the fits in FIG. 4B by the slope obtained using a linear complex containing a single dye: the P(1, 1,1) complex.

Example 3

Regulated Immunofluorescent Protein Intensities

A primary antibody and a DNA-conjugated secondary antibody were used to couple ssDNA tags to stathmin, a microtubule regulatory protein. DNA strand displacement reactions were then performed to assemble reporting complexes possessing between 1 and 9 Cy3 molecules. Complexes containing 3 and 9 Cy3 molecules were generated using linear labeling probes possessing 1 or 3 dye molecules by reacting with single branched DNA complex that had already been complexed to the DNA-Ab conjugates.

Figure 5A:
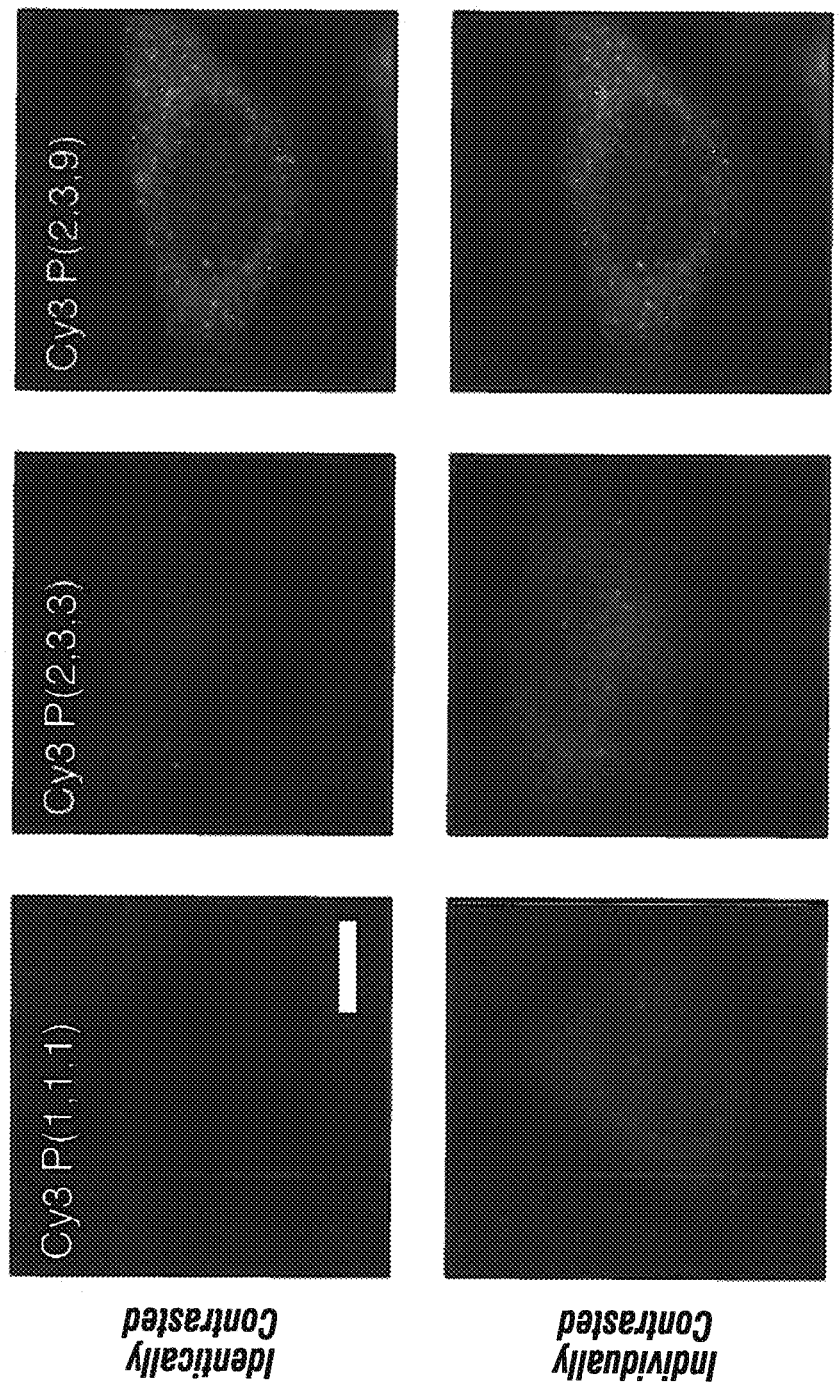
FIGS. 5A-C.

FIG. 5A, top row shows the images of the Cy3-labelled probes systems (P(1,1,1), P(2,3,3), P(2,1,9) with amplification ratios of 1×.3×.9× respectively). Equally contrasted images in the top row and the same images are contrasted individually in the bottom row.

Figure 5B:
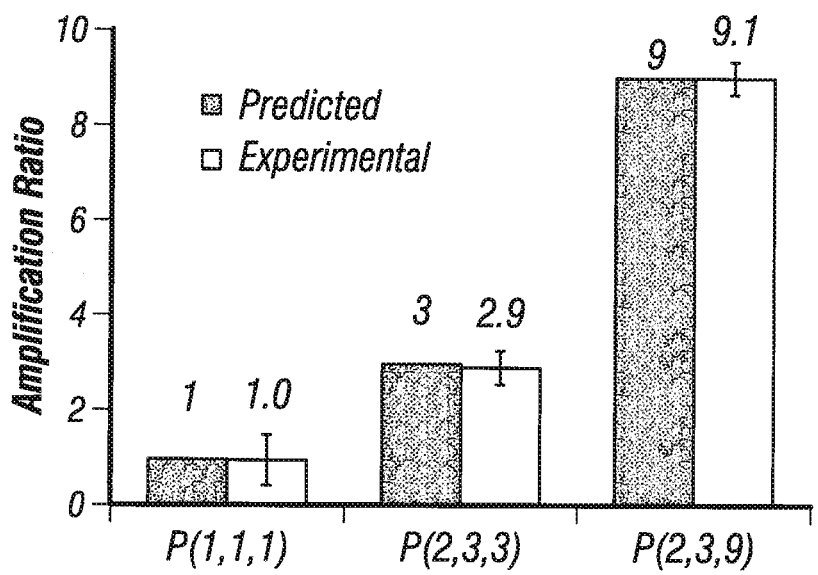
Figure 5C:
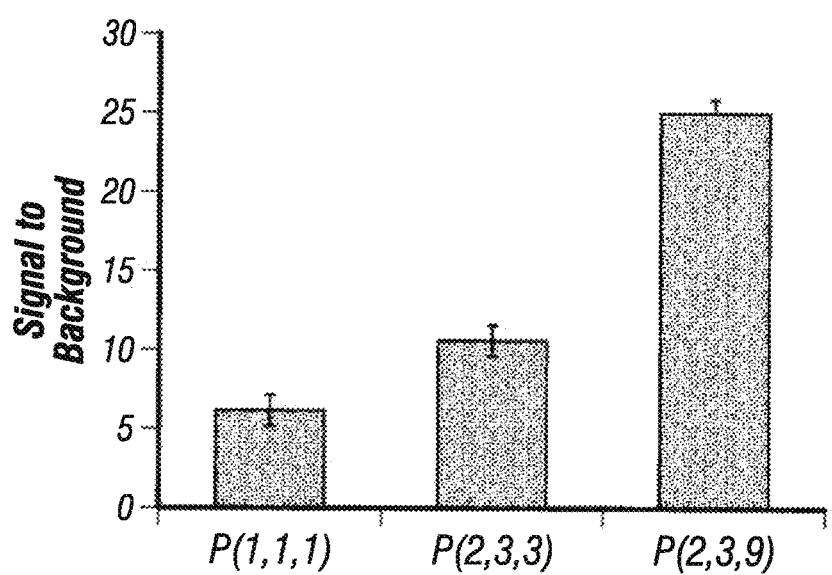

FIG. 5B shows comparisons of theoretical and measured amplification ratios for modular probes targeting antibodies. Theoretical amplification ratios indicate the maximum number dyes that can be integrated into a complex. Experimental amplification ratios are based on the intensity of the cytoplasmic regions of approximately 10 cells taken at the same conditions for each probe system as compared to the intensity of the single dye: the P(1, 1,1) complex.

Example 4

Detection of Multiple Targets Via CTS and Storm Imaging

Color-time sequence (CTS) codes for each protein target will be defined using dynamic DNA complexes that incorporate different pairs of fluorescent dye molecules that are suitable for use in STORM procedures (e.g., Alexa Fluor 488-Alexa Fluor 647). Pulsed laser excitation of the blue-shifted dyes in the complex (e.g., Cy2, Alexa488, Cy3) will activate a corresponding red-shifted dye (Alexa647 or Cy7) within the complex, which will be imaged in one of two channels of the fluorescence microscope.

Color-time sequence codes for each protein target will be generated as follows: a set of DNA complexes for each target will be prepared such that each complex in a set is specific that particular target (i.e. contains the same polynucleotide region that is substantially complementary to the polynucleotide on the target-specific recognition agent) but different dye pairs suitable for STORM imaging. Pulsed laser excitation of the blue-shifted dyes in the complex (e.g., Cy2, Alexa488, Cy3) will activate a corresponding red-shifted dye (Alexa647 or Cy7) within the complex, which will be imaged in one of two channels of the fluorescence microscope.

Figure 6:
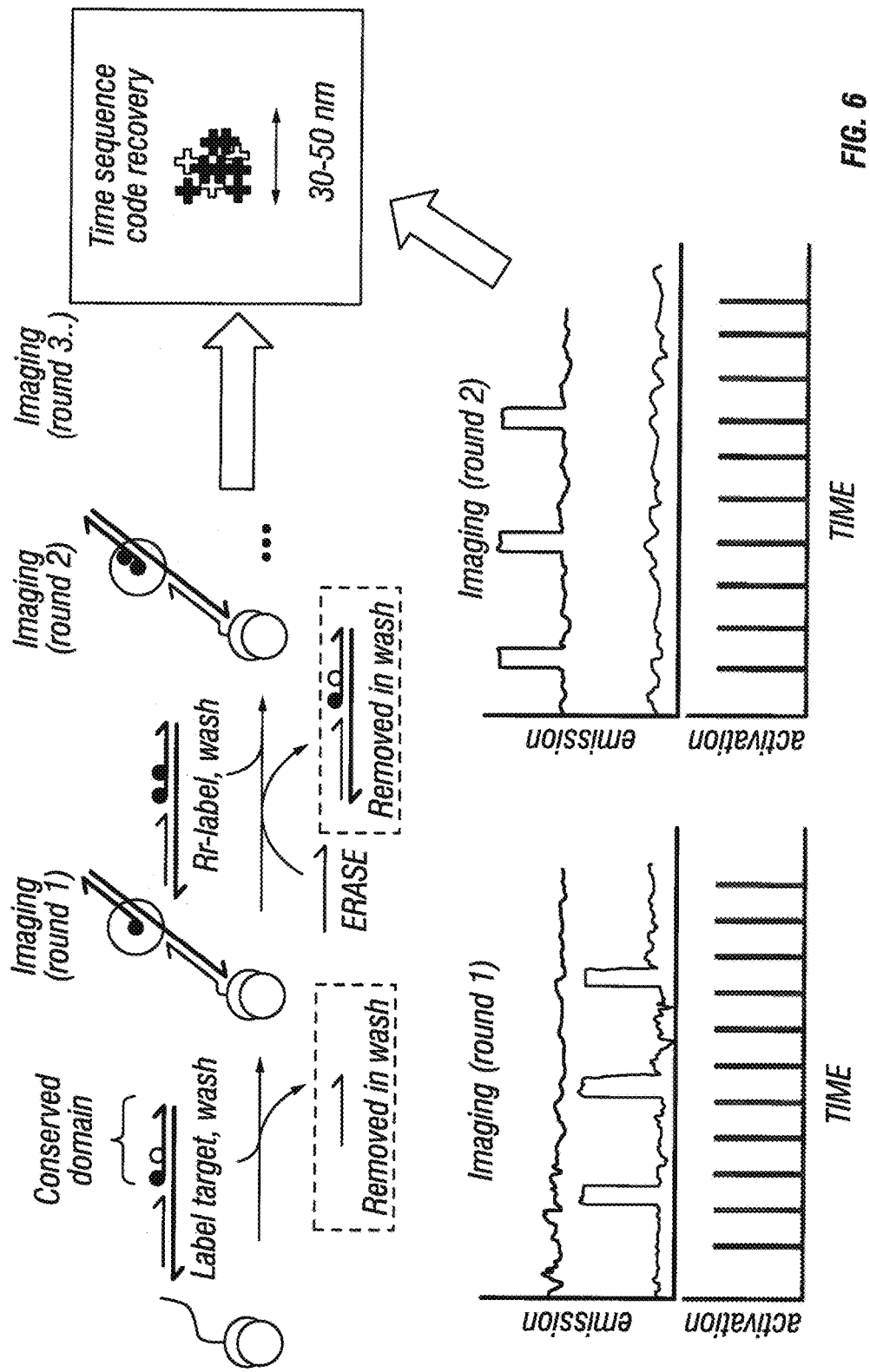
FIG. 6.

During acquisition of the STORM images, each target in the sample will be labeled and relabeled with the set of DNA complexes in a predetermined order, thereby causing the color of the target to change in time as STORM images are acquired, yielding a CTS code specific to each target (see FIG. 6).

The foregoing detailed description has been given for clearness of understanding only and no unnecessary limitations should be understood there from as modifications will be obvious to those skilled in the art.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

The disclosures, including the claims, figures and/or drawings, of each and every patent, patent application, and publication cited herein are hereby incorporated herein by reference in their entireties.

What is claimed:

1. A method for modulating the reporting intensity of a labeled target in a sample of fixed cells or tissues, the method comprising:

complexing a target-recognition agent to the target, wherein the target-recognition agent comprises a first polynucleotide, to form a first polynucleotide-target complex;

reacting the first polynucleotide-target complex via strand displacement with a branched or dendritic dynamic DNA complex to create a dynamic DNA-target complex;

reacting the dynamic DNA-target complex via strand displacement with a first probe comprising at least one dye and a second polynucleotide to form a first labeling complex;

measuring the reporting intensity of the first labeling complex; and contacting the sample with a second probe comprising at least one dye and a third polynucleotide, wherein the second probe displaces the first probe via strand displacement to form a second labeling complex;

wherein the second probe carries a different number and/or type of dye molecule than the first probe.

2. The method of claim 1, wherein at least one dye is a fluorescent dye.

3. The method of claim 1, where at least one probe comprises at least two dye molecules.

4. The method of claim 3, wherein the at least two dye molecules are the same dye.

5. The method of claim 3, wherein the at least two dye molecules are different dyes.

6. The method of claim 1, wherein the first probe and the second probe comprise different dyes.

7. The method of claim 1, wherein the first labeling complex and the second labeling complex have a 36:1 to 1:36 ratio of dye molecules.

8. The method of claim 1, wherein the first labeling complex and the second labeling complex have a 9:1 to 1:9 ratio of dye molecules.

9. The method of claim 1, wherein at least one polynucleotide is at least one selected from a group consisting of DNA and RNA.

10. The method of claim 1, wherein the target-recognition agent comprises at least one antibody, peptide, aptamer, enzyme, or self-assembling protein.

11. The method of claim 1, wherein the first polynucleotide comprises a region that binds to the target.

12. The method of claim 1, further comprising measuring the reporting intensity of the second labeling complex.

\* \* \* \* \*

UNITED STATES PATENT AND TRADEMARK OFFICE
CERTIFICATE OF CORRECTION

PATENT NO. : 10,150,988 B2
APPLICATION NO. : 14/421504
DATED : December 11, 2018
INVENTOR(S) : Michael Diehl et al.

Page 1 of 1

It is certified that error appears in the above-identified patent and that said Letters Patent is hereby corrected as shown below:

On the Title Page

Item (54) and in the Specification, Column 1, Lines 1-4, delete "SINGLE" and replace with --SIGNAL-- therefor.

Signed and Sealed this
Twenty-eighth Day of May, 2019

Andrei Iancu
*Director of the United States Patent and Trademark Office*